US012329215B2

(12) United States Patent
Kaltenbach

(10) Patent No.: US 12,329,215 B2
(45) Date of Patent: Jun. 17, 2025

(54) DEVICE FOR PROTECTION AGAINST CONTAMINATION

(71) Applicant: Forstgarten International Holding GmbH, St. Gallen (CH)

(72) Inventor: Stefan Kaltenbach, Rebstein (CH)

(73) Assignee: Forstgarten International Holding GmbH, St. Gallen (CH)

( * ) Notice: Subject to any disclaimer, the term of this patent is extended or adjusted under 35 U.S.C. 154(b) by 592 days.

(21) Appl. No.: 17/315,728

(22) Filed: May 10, 2021

(65) Prior Publication Data

US 2021/0345706 A1 Nov. 11, 2021

(30) Foreign Application Priority Data

May 11, 2020 (DE) .......................... 102020112737.5

(51) Int. Cl.
| | | |
|---|---|---|
| A41D 13/11 | (2006.01) | |
| A61B 90/00 | (2016.01) | |
| A61B 90/30 | (2016.01) | |
| A61B 90/35 | (2016.01) | |
| A61B 90/50 | (2016.01) | |

(52) U.S. Cl.
CPC .......... *A41D 13/1184* (2013.01); *A61B 90/05* (2016.02); *A61B 90/30* (2016.02); *A61B 90/35* (2016.02); *A61B 2090/502* (2016.02)

(58) Field of Classification Search
CPC ............ A41D 13/1184; A41D 13/1161; A61B 90/05; A61B 90/30; A61B 90/35; A61B 2090/502; A61F 9/02; A61F 9/025; A61F 9/029; A61F 9/04; A61F 9/045; A61F 9/06; A61F 9/064; A61F 9/065; A62B 18/082; A42B 3/22
See application file for complete search history.

(56) References Cited

U.S. PATENT DOCUMENTS

| | | | |
|---|---|---|---|
| 4,944,294 A | 7/1990 | Borek | |
| 4,965,887 A | 10/1990 | Paoluccio | |
| 5,206,956 A | 5/1993 | Olson | |
| 5,341,513 A * | 8/1994 | Klein | ........................ A61F 9/02 |
| | | | 128/857 |
| 5,471,679 A * | 12/1995 | Paoluccio | .............. G02C 11/00 |
| | | | 2/9 |
| 5,692,522 A | 12/1997 | Landis | |

(Continued)

FOREIGN PATENT DOCUMENTS

| | | | | |
|---|---|---|---|---|
| DE | 19983185 T1 | 5/2001 | | |
| DE | 202020101699 U1 * | 5/2020 | ............. | A61B 90/50 |

(Continued)

OTHER PUBLICATIONS

Translation of DE-202020101699-U1 (Year: 2020).*

*Primary Examiner* — Keri J Nelson
*Assistant Examiner* — Seth R. Brown
(74) *Attorney, Agent, or Firm* — McDonnell Boehnen Hulbert & Berghoff LLP

(57) ABSTRACT

The present invention relates to a protective shield which is attached to a mouthguard/which is attached to at least one coupling element which is attached to a pair of glasses or to a mouthguard, the protective shield covering the mouth area and also the eye area and the area of the front cheeks and extending from below the mouth to above the eyebrows.

12 Claims, 21 Drawing Sheets

(56) References Cited

U.S. PATENT DOCUMENTS

| | | | | |
|---|---|---|---|---|
| 2011/0145978 A1* | 6/2011 | Harbin | ............... | G02B 27/0176 |
| | | | | 2/209.13 |
| 2012/0131730 A1* | 5/2012 | Shoham | ................ | B29C 51/422 |
| | | | | 2/9 |
| 2016/0353815 A1* | 12/2016 | Nabai | ..................... | A61B 90/05 |
| 2018/0177251 A1* | 6/2018 | Yoo | ................... | A41D 13/1184 |
| 2021/0259347 A1* | 8/2021 | Lambert | ............ | A41D 13/1161 |
| 2021/0329998 A1* | 10/2021 | Crooks | .................... | G02C 9/04 |
| 2022/0117788 A1* | 4/2022 | Anderson | ............... | A61B 90/05 |

FOREIGN PATENT DOCUMENTS

| | | | | |
|---|---|---|---|---|
| EP | 1045651 B1 | 7/2002 | | |
| EP | 0957993 B1 | 3/2007 | | |
| WO | 198910106 A1 | 11/1989 | | |
| WO | WO-2004083941 A1 * | 9/2004 | ............. | A61F 9/025 |

* cited by examiner

DEVICE FOR PROTECTION AGAINST CONTAMINATION

FIELD OF INVENTION

The invention relates to a shield-like or screen-like device for protecting, for example, against laser radiation and/or against contamination of breathing masks or mouth-nose masks, of wearers of such mouth-nose masks and of patients. In particular, the device comprises fixing the shield with respect to the mouth-nose mask or respirator and fixing optical or electronic devices such as lamps, lenses or cameras to the protective shield.

STATE OF THE ART

U.S. Pat. No. 4,944,294 (Borek 1988) describes a surgical face mask with mouth-nose protection and a transparent splash shield at the top of the nose bridge and below the eyes, which covers the eyes and eyebrows. Here, the filter area in front of the mouth and nose is freely accessible for contamination and this is the hygienic problem.

Very similar is patent specification WO/89/10106 (Russel 1988), which also ties a transparent splash shield above the mouth-nose mask, with the same problem of contamination of the filter itself, through which contaminated aerosol is then inhaled.

With some changes in detail, the patent specification EP 1 045 651 B1 also pursues the goal of attaching an eye shield as splash protection above the mouth-nose guard of a surgical mask, in particular with lateral attachment. Here, too, the shield covers only the eye area above the cheeks and not the mouth-nose area, see in particular FIGS. 1 and 4a of EP 1 045 651 B1.

Consequently, all of these prior art inventions do not provide protection against contamination of the filter fabric itself because the splash shields do not cover the filter fabric.

So far, only solid protective masks such as those shown in EP0957993B1 would provide the desired full protection. However, these masks are very heavy and very uncomfortable to wear, which is unacceptable for a dentist or surgeon as well as for the patient.

Consequently, given the existing state of the art, there is a high risk that the mask wearer protects himself with a supposedly safe FFP3 mask, but then contaminates the patient via the exhalation valves without filter protection by aerosol ejection and accompanying condensate splashes.

TASK OF THE INVENTION

It is the task of the invention to achieve significantly better protection, in particular of the mouth-nose area, the chin and the cheeks against contamination, by means of a moisture-impermeable protective shield. A further object of the invention is to achieve improved protection of the eyes from, for example, laser radiation. This is preferably to be achieved with low weight, good wearing comfort, yet low breathing resistance and good visibility and communication. In particular, the task is to cover the mouth-nose area with a shield that diverts and at least reduces the transport of droplets and aerosols between wearer and counterpart, thereby reducing its contamination. This shield should also cover the eyes and the lower forehead.

SUMMARY OF THE INVENTION

The technology according to the invention is described by the features according to the independent claims. Further optional features of embodiments are described in the subclaims.

According to a first aspect of the invention, an arrangement for protecting the face of a wearer, for example from contamination or laser radiation, is proposed, comprising a shield (protective shield, face shield) which is attachable to an auxiliary means, and a connecting means via which the shield is attachable to the auxiliary means. The use of an auxiliary means is enabled by the protection against contamination or laser radiation by the shield under improved conditions.

Preferably, the auxiliary means comprises a mask, in particular a respirator mask. The mask may comprise a filter, in particular an air filter. The auxiliary means may further be formed as a head frame, in particular as glasses, in particular as magnifying glasses. Alternatively or cumulatively, the auxiliary means may be configured as a cap, in particular a baseball cap. The shield is particularly advantageous for medical practitioners who can combine the auxiliary means required for treatment with the shield, or are protected from contamination and/or laser radiation by the shield during the use of the auxiliary means in the course of treatment.

In a preferred embodiment, the connecting means comprises a light-emitting means and/or a camera and/or a connector and/or an end cap. The light-emitting means can illuminate a working area, and the camera can record the working area at the same time. The light-emitting means can be controlled according to position and direction, in particular to activate them only when the beam hits the appropriate areas. In addition to light source, the light-emitting means can include electronics, sensors, accumulators and contacts, and conductive elements, and they can be rechargeable or contain exchange batteries or be connected with cables to battery housings or power sources. The shield is thus particularly advantageous for medical professionals who can combine the connecting means needed for treatment with the shield, and furthermore are protected from contamination and/or laser radiation by the shield while using the connecting means as part of a treatment.

In a preferred embodiment, the connecting means is attachable to the auxiliary means via the shield by means of a reversible connection. The reversible connection may comprise a button connection, a Velcro connection, a toggle connection, or a magnetic connection. In a preferred embodiment, the connecting means and the auxiliary means each have at least one magnet between which the shield can be arranged, in particular held, in particular clamped.

A reversible connection is advantageous because the shield can be removed for cleaning or also for attachment to another auxiliary means. Furthermore, removing the shield frees up access to the auxiliary means, for example the mask, so that the mask can also be changed separately. The coupling elements of the auxiliary means can also be combined with their fastenings for the tensioning elements or pull straps that lead to the ears or behind the head. This is advantageous because no additional fastenings are required on the auxiliary means.

In a preferred embodiment, the arrangement has an intermediate member, wherein the shield can be arranged between the connecting means and the intermediate member. Preferably, the connecting means and the auxiliary means and/or the intermediate member each have at least one magnet between which the shield can be arranged, in particular held, in particular clamped. In this case, the connecting means can be arranged on the shield independently of the auxiliary means. In this case, the intermediate member is arranged on the side of the shield facing the wearer, advantageously arranged near the forehead so that vibrations acting on the shield can be compensated by contact of the forehead with the intermediate member. The intermediate member can be a spacer.

In a preferred embodiment, the intermediate member has a first longitudinal end at which a first magnet is disposed and a second longitudinal end at which a second magnet is disposed, wherein the first magnet is adapted to interact with the magnet of the auxiliary means, and wherein the second magnet is adapted to interact with the magnet of the connecting means, such that the shield is clampable between the connecting means and the intermediate member via a magnetic connection and the intermediate member is clampable between the shield and the auxiliary means via a magnetic connection. The intermediate member can be a spacer, which can be arranged between the shield and the auxiliary means. This enables a reversible connection both between the connecting means and the intermediate member and between the intermediate member and the auxiliary means.

Advantageously, the shield has a recess. The additional recess in the shield can be used for magnetic clamping. For this purpose, a magnet is attached to both sides of the shield so that the shield is clamped between the magnets. By making a recess in the shield at the point where the shield is clamped between the magnets, the magnetic attraction force between the magnets can be increased, and thus the clamping can be strengthened. In the area of the recess, the shield may be thinned and/or interrupted. Thinned means that the shield is formed thinner there than in other areas of the shield.

In a preferred embodiment, at least one magnet is arranged in the recess and can interact with a magnet of the connecting means and/or a magnet of the intermediate member or of the auxiliary means to clamp the shield between the connecting means and the intermediate member/auxiliary means. The at least one magnet can be glued into the recess and thus be permanently connected to the shield.

In a preferred embodiment, the arrangement has a spacer that can be arranged between the shield and the auxiliary means. This allows better air circulation between the auxiliary means, for example the mask, and the shield. Spacing of the shield from the mask can be achieved by a spacer defining a distance between the shield and the mask. The spacer may also be disposed between the shield and the air filter. The mask may include filter elements for filtering air. The filter elements may be fabric or non-woven fabric or foam mats or granules, and the filters may be monodirectional or multidirectional.

The shield can be coupled to the side, bottom and or top of a gas permeable hood with filtering action to provide even more protection from contamination.

The mouth-nose filter (see FIG. 3a or 4a) can optionally include active breathing support e.g. electrical ventilation during inhalation.

The mouth-nose filter can contain blow-out valves from which the exhaled air escapes in the event of overpressure in the mask. These are preferably located behind the shield and thus the exhaled air preferably does not flow to the patient or the counterpart.

The inhaled and or exhaled air can be deflected by the shield so that it does not flow directly to a counterpart or to the patient, but laterally or up and or down.

In a preferred embodiment, the spacer can be located between the shield and the forehead of the wearer. Likewise, spacers can be attached to the mask. This can avoid vibrations. Vibrations can affect the light spot of a lamp or the image focus of a camera.

In a preferred embodiment, the shield can be held, in particular clamped, between the spacer and the auxiliary means. Preferably, the spacer has a magnet at both ends so that one end can be magnetically connected to the auxiliary means and the other end can be magnetically connected to the side of the shield facing the wearer.

In a preferred embodiment, the connecting means is directly attachable to the auxiliary means. For example, the connecting means, i.e., the camera or a light-emitting means, can be attached directly to the glasses.

This reduces the overall weight of the shield to be worn, and avoids the effect of a torque acting on the shield, caused by a connecting means attached to the shield.

In a preferred embodiment, the connecting means can be arranged on the side of the shield facing away from the carrier. In this embodiment, the shield is arranged between the wearer and the connecting means. The connecting means, which may be a camera or a light-emitting means, thus has a direct view of the object to be viewed, while the shield protects the wearer from contamination or laser radiation.

In a preferred embodiment, the auxiliary means can be arranged between the wearer's face and the shield. This protects the auxiliary means against contamination.

In a preferred embodiment, the shield has a one-dimensional or two-dimensional curvature. The shield can be predominantly one-dimensionally curved in the shape of a cylinder lateral surface, i.e. bent from a film, as shown in FIGS. 4a and 4b. This results in high mechanical stability in the shield against bending about the transverse axis, i.e. good stabilization of the lamps or cameras mounted at the top. Even more stable and better fitting are two-dimensionally curved masks, such as can be produced from films by thermoforming. Depending on the material and film thickness, the stability is more or less. In a preferred embodiment, the shield has a thermoformed foil, wherein the thermoformed foil determines a basic shape of the shield. The shield may also be in the form of a sheet of foil. The shield can likewise be formed in a shell shape or have beveled flat areas.

In a preferred embodiment, the shield has a one-dimensional or two-dimensional curvature. The shield can be predominantly one-dimensionally curved in the shape of a cylinder lateral surface, i.e. bent from a film, as shown in FIGS. 4a and 4b. This results in high mechanical stability in the shield against bending about the transverse axis, i.e. good stabilization of the lamps or cameras mounted at the top. Even more stable and better fitting are two-dimensionally curved masks, such as can be produced from films by thermoforming. Depending on the material and film thickness, the stability is more or less.

In a preferred embodiment, the shield has a size such that the shield attached to the first auxiliary means can extend over the face of the wearer who is wearing the first auxiliary. This protects the auxiliary means, but in particular the face of the wearer, from contamination. Advantageously, the shield has a size such that the shield can extend over the entire face of the wearer so that contamination of, for example, the eyes is also avoided. The width of the shield can be elastically adapted to the width of the head. The necessary adaptation results from the dimensions of the mask, the position of the coupling elements and also usable spacers, which can be arranged between the shield and the auxiliary means or between the shield and the forehead area of the wearer.

In a preferred embodiment, the shield is impermeable to liquids. In the course of treatment of patients, contamination of a doctor by droplets from the patient, such as occurs during dental treatment, is possible. Therefore, it is advantageous if the shield is impermeable to liquids.

In a preferred embodiment, the shield has at least one transparent section, the transparent section being arranged in particular in the field of view. For use in the medical field, it is necessary that particularly the field of view of the shield is transparent. In this case, the shield is transparent at least in the eye area and is designed with high optical quality and low interference so that the field of view is only slightly impaired. The shield can also be transparent over the entire area. It is also advantageous if the field of view is of high optical quality.

In a preferred embodiment, the shield has polycarbonate or an acetate film. Another sufficiently mechanically stable and transparent plastic can also be used. Shields made of gorilla glass in the viewing area are also possible so that a high optical quality is achieved when viewing through the shield.

In a preferred embodiment, the shield has an anti-reflective coating and/or an anti-fog coating, each of which is arranged on the side facing the wearer. These coatings ensure a clear view for the wearer through the shield or at least through the transparent area of the shield.

In a preferred embodiment, the shield has a thickness of 0.10 mm to 0.8 mm, particularly preferably between 0.20 mm and 0.50 mm. A low thickness allows the shield to be easily bent into the desired shape for attachment to the auxiliary means and results in a correspondingly low weight.

In a preferred embodiment, the shield has a weight of between 4 and 60 grams, particularly preferably between 10 and 30 grams. The low weight enables the shield, which is attached to a breathing mask or magnifying glasses, to be worn comfortably, even over a longer period of time, as may occur during operations.

In a preferred embodiment, the shield is made in one piece from impact-resistant material such as polycarbonate or physically or optically similar plastics. This avoids joints that can become brittle over time.

In a preferred embodiment, the shield is stable in shape under its own weight or the shield conforms to a planar support surface under its own weight, being brought into at least one-dimensional flexure by fastening elements in the fastened state.

In a preferred embodiment, the shield has one or more coupling elements by which the shield can be coupled or attached to the auxiliary means in addition to the connecting means. The coupling elements may be, for example, hooks on an inner side of the shield that can be hooked into temples of a glasses frame so that the glasses frame mechanically supports the shield.

The shield can be fastened at the front center with coupling elements and/or placed on the forehead. The shield can be fastened by coupling elements that include snaps or toggles or Velcro or magnets.

The coupling elements may be combined with the fasteners for the tension elements or tension straps leading to the ears or behind the head.

The coupling elements on the shield can be mechanically reversibly detachable from their counterparts on the mask to allow the shield to be removed, especially when it is necessary to reach and change the mouth-nose guard.

In a preferred embodiment, the shield is a shield for protection from laser radiation, in particular for protection of the eyes from laser radiation.

In a preferred embodiment, the shield is made of or comprises acrylic.

In a preferred embodiment, the shield is configured such that the shield reduces a given laser radiation to a non-hazardous level, for example, to a non-hazardous level according to EN207:2009 or EN208:2009. For example, the shield has one or more of the following optical densities: 6 at 190-315 nm, 6 at 315-440 nm, 3 at 750 nm-1120 nm, 4 at 770-1100 nm, 5 at 785-1100 nm, 6 at 800-1090 nm, 6 at 10600 nm. The values indicated with nanometers are the wavelengths of laser radiation. The optical density value indicates by how many powers of 10 the radiation intensity is reduced when passing through the shield.

Alternatively or additionally, the shield may have one or more of the following protection levels, for example, according to EN207:2009: D LB6 IR LB3 at 190-315 nm, DIR LB6 at 315-440 nm, DIR LB3 at 750-1120 nm, DIR LB4 at 770-1100 nm, DIR LB5 at 785-1100 nm, DIR LB6 at 800-1090 nm, DI LB3 at 10600 nm.

In a preferred embodiment, the shield has a daylight transmission of at least 40% or at least 50%. Alternatively or additionally, the shield may have a daylight transmission of at most 70% or at most 60%. For example, the shield has a daylight transmission of 55%.

In a preferred embodiment, for example when the shield is a shield for protection against laser radiation, it has a thickness between 2.5 mm and 4 mm inclusive, for example between 3 mm and 3.5 mm inclusive. For example, the thickness is 3.2 mm. The shield may be colored green in the eye area.

In a preferred embodiment, the shield includes a lower and/or an upper protective section. The lower and/or upper protective section may extend from a main section of the shield toward the wearer. In particular, the main section is disposed between the lower and upper protective sections. The lower and/or upper protective section may extend transversely or perpendicularly to the main section. The main section is arranged to cover the eye area of the wearer, for example, and is thus arranged at the level of the eyes when the shield is worn. The lower protective section is arranged below the eyes when the shield is worn. The upper protective section is arranged above the eyes when the shield is worn. The lower protective section may have a recess for the nose of the wearer such that the nose is arrangeable in the recess. The lower protective section is arranged, for example, so that it is guided below the eyes of the wearer as close as possible to the face of the wearer, in particular is guided closer to the face of the wearer than the main section. The same may apply to the upper protective section.

SPECIAL BENEFIT OF THE INVENTION

The invention improves hygiene and protection against contamination and/or laser radiation, especially for doctors or dentists who treat patients. In particular, it improves protection against contamination by splashes and or aerosol transfer from the wearer of the mask to the patient or the person opposite. This is all the more important because conventional FFP2 or FFP3 standard breathings masks have blow-out valves and these mostly unfiltered valve outlets do not prevent the transfer of aerosol from the wearer of the mask to the patient. This is where the protective screen of the invention acts by intercepting splashes and redirecting the airflow. Thus, the invention produces significantly improved patient protection and wearer protection. The invention also includes the mechanical connection between this protective shield and the mouth-nose mask, and also between the protective shield and attachable accessories, such as a lightweight LED light clamped to the top of the shield to illuminate the surgical area. It should be emphasized that the protective shield also prevents contact with the mask and, in particular, the air-aspirating filter area itself. Taken together, this means far greater protection for the wearer of the mouthguard. Due to the interposed shield which allows a comparatively unimpeded supply of breathing air, air resistance is not measurably increased during inhalation and also during exhalation. This is particularly advantageous for long periods of wear. Nevertheless, the protective shield and the modified airflow prevent exhaled aerosol from hitting the patient directly, which provides better protection for the patient or the person opposite in particular and reduces the formation of contaminated aerosols overall. In conjunction with good mouth-nose protection, this provides very good protection against contamination while at the same time having very little impairment of vision and breathing and communication.

The proposed solution comprises a protective shield against contamination and/or laser radiation, which covers the mouth-nose area and also the eye area. The protective shield is preferably attached directly to the breathing mask or the mouth-nose guard with fastening elements or via spacers.

In the following, the term mouth-nose guard is used for the group of textile surgical masks, mouth-nose masks sealing with rubber elements and breathing masks formed directly to the individual mouth-nose area and other variants, regardless of which protection class FFP1, FFP2, FFP3 or without FFP certificate these devices have.

The core of the invention's benefit is the bidirectional protection against droplet transfer and aerosol transfer, which takes place without additional shields. The contamination risk to be reduced includes in particular the transport of contamination material by hands on the mouth-nose guard and on the facial area including eyes and partially chin, cheeks, lower forehead.
 by drops or splashes or aerosols from the patient, especially from the treatment area onto the wearer of the mask or onto the mask, especially in the area of the air inlet.
 from the wearer of the mask to his hands or instruments, in particular from the area of the air outlet to the treatment instruments and/or the apparently sterile gloves.
 by drops or splashes or aerosols from the wearer of the mask onto the patient or opposite person, in particular from the area of the air outlet.

The air inlet and air outlet are always located at an outlet of the mouth-nose guard, which is between the patient and the wearer of the mask and within the range of movement of the hands.

One aspect of the disclosure comprises a preferably lightweight and thin yet sufficiently mechanically robust protective shield. In this aspect, the releasable fastening of the protective shield preferably takes place at a plurality of appropriately prepared support points directly on the mouth-nose guard. This fastening ensures a constant alignment relative to the head position, namely as far as the mask is fastened relative to the head position. In the event that the protective shield alone is connected to the mouth-nose guard, the protective shield moves with the mouth-nose guard. In the case where the shield is connected to another head support device, it moves with that head support frame, which may be glasses or a head-mounted brace. In the case that the shield is connected to both mouth-nose guard and a head support frame such as glasses, the result is a particularly stable fixed position of the protective shield relative to the head. This has mechanical and optical advantages, especially as soon as accessories such as lightweight LED lights are attached directly to the protective shield.

The difference to the prior art becomes clear as soon as one compares the previous arrangements (see FIG. 1a) with the arrangement according to the invention in a very simple embodiment (see FIG. 2a). According to the prior art, a small protective shield covers the eye area completely and the lower part of the forehead partially, but not the area of the mouth-nose guard and its surroundings. Unfortunately, however, these lower areas are particularly exposed to the risk of contamination.

The proposed improved solution covers in particular the mouth-nose area and its surroundings and furthermore also the eye area and at least partially the forehead of the wearer of the mask. Another special feature is that the shield is attached directly to the mouth-nose guard or to the breathing mask, preferably via detachable fastening points, which can be of Velcro-type adhesive, magnetically adhesive, hole-type or mechanically keyed design. It is known to attach a transparent protective screen to the top of an surgery mouth-nose guard, e.g. via a connecting seam. However, according to the invention, a visor is coupled here, preferably reversibly detachable and re-couplable, whereby the visor covers at least the mouth-nose area and the eyes and part of the surrounding face over a large area. The visor or protective shield, respectively, can be partially flat or curved over a large area in at least one direction or, if necessary, curved in two spatial directions and thus pulled back under the chin towards the neck to achieve better protection and better deflection of the breathing air. This can be particularly useful for dentists, because here the splashes come mainly from the patient's mouth and can otherwise fly from below past the shield to the face and mask of the wearer of the mask.

FIG. 1 a shows the prior art with a transparent protective shield 20 attached directly or laterally above the mouth-nose guard. However, this shield only covers the eyes and eyebrows, but not the mouth-nose area itself. Incoming drops and aerosols can therefore contaminate the mouth-nose guard 10 and the filter material 11.

The improved contamination protection is characterized by the fact that the protective shield is located in front of the mask or the mouth-nose guard, respectively, and diverts the path of the breathing air as far as it is not filtered by the filter, i.e. when coughing and in the case of existing exhalation valves on the mask. This ensures that contamination can be better reduced or prevented.

The desired effect may be achieved by various embodiments and various combinations of embodiments.

In a preferred embodiment, the protective shield is approximately cylindrically curved, i.e. it has been bent from a flat planar sheet and is stabilized in the curved shape by mechanical holding elements. This can result in additional slight bending in further directions of curvature, but this is to be understood as an evasive distortion of the bent flat element.

In another very preferred embodiment, depending on the application, the protective shield is curved in two spatial directions, i.e. curved in the shape of a shell like an ellipsoid section. This shape creates an inherent mechanical stability of the protective shield, but can additionally be mechanically braced by holding elements and adapted in geometry to the head and mouth-nose guard, which further increases the mechanical stability.

In a preferred embodiment, the protective shield is attached to the mouth-nose guard via at least three, preferably at least four, contact points or contact areas, thereby achieving sufficient distance from the face so that breathing air can flow and preferably also so that mimic facial movements do not cause the protective shield to move. In a particularly preferred embodiment, this is achieved by fastening elements which may have spacers and or which are raised above the surrounding regions of the mouth-nose guard.

In another preferred embodiment, the protective shield is coupled in the upper region by mechanical coupling points to a head frame, in particular glasses that are mechanically stable on the head, e.g., magnifying glasses such as are often worn by dentists. In this case, the protective shield preferably runs at a small distance in front of the optics of the magnifying glasses so that vibrations of the shield are not transmitted to the magnifying optics. In an extended embodiment, the distance of the protective shield in front of the head frame and possibly in front of the loupe optics is achieved by a mechanically stable coupling spacer, which is coupled to the upper head mount, in particular to the glasses frame. The mechanical coupling to the glasses frame is preferably achieved by means of a magnetic connection encoding in six spatial dimensions (three translation and three rotation) in relative terms or by other similarly acting connecting elements. Thus, the spacer is proximally attached to the upper head mount/glasses frame and distally supports the protective shield, in particular by a counter-retaining clamping element that generates a clamping force to the spacer that can hold the shield. At this point, the shield consists of a thin layer of glass or plastic or other film. In the preferred case, the mechanical clamping force is sufficient to hold the foil without further retention elements and to sufficiently secure it not only against slipping but also against twisting. In another embodiment, mechanical retentions and/or apertures through the shield are provided at the clamping point to fix the mechanical fixation relative to the head mount and in particular in position relative to the head of the wearer of the mask.

In one group of embodiments, the protective shield is attached to the mask directly or via spacers. FIG. 2a. shows a simple form with textile, mesh, non-woven or fabric filter. The mouth-nose guard is attached to the ears, for example, or to the head with straps. The shield 30 is attached to the mouth-nose guard.

FIG. 3a also shows an attachment of the shield to a breathing mask and likewise FIG. 4a. As a special feature, FIG. 3a has the shield 30 attached to the attachment piece 47 of the filter cartridge by means of opening 37. The mouth-nose portion of the mask itself, which carries the filter cartridge and shield, is attached to the head or ear by means of strap elements, etc.

FIG. 4a shows another embodiment with adaptable or 3D adapted rim and a stable frame element which supports a filter area at the front, whereby the filter mats are exchangeable. Fixing elements for the retaining straps 15 are provided on the side of the mouth-nose mask.

These embodiments have in common that a mechanical chain of connections is built up, which ultimately attaches the mask or the mouth-nose guard, respectively, to the head and the protective screen at least at several support points on the mask/mouth-nose guard. Further support points directly or via mechanical spacer elements on the head are possible, usually also helpful for stabilization against vibrations, but not absolutely necessary.

In a further embodiment, see FIGS. 3a, 3b and 3c, the protective shield comprises an opening which is at least 10 mm in diameter and can accommodate a connecting element or adapter piece through which at least part of the breathing air can flow and to which a filter element can be coupled distally, which is preferably designed to be replaceable. In the vicinity of the breakthrough through the protective shield, at least three contact points are present or a flatly extended contact area, preferably in a round, oval or partially round-cornered ring shape, by means of which a mechanical holding force is achieved between the mouth-nose guard and the protective shield. This holding force or the holding moments stabilize and fix the protective shield relative to the front distal region of the mouth-nose guard in the vicinity of the connecting element. In a further developed embodiment, the mouth-nose guard can be stabilized in the region of the connecting element by internal and hygienically covered lightweight structures, in the sense of a spongy or trabecular filled body with a compact shell, this region merging into a circumferential region which is elastically or plastically partially adaptable in shape, which assumes the sealing function and which encloses the mouth-nose region. The combination of these embodiments achieves a very good and long-term comfortable tightness of the mouth-nose guard on the face of the wearer and at the same time a very good mechanical stability of the connection area to the protective shield and, if necessary, to the filter element. The mechanically stable and well-sealing mouth-nose guard is fastened to the wearer's head by sufficiently strong tension strap elements, whereby a head strap with a branched strap design is preferred in order to prevent slipping off the back of the head. Fastening the tension straps to the wearer's ears is possible but generally less resilient and consequently not quite as positionally stable, so this is only considered for particularly lightweight embodiments or in combination with further head-mounted support elements such as glasses with coupling of the protective shield to additional support points.

FIG. 5a shows a shield with a special fastening technique not directly to the mask, especially for the case of mechanically unstable mouth-nose masks. The shield is preferably held centrally above the center of the eye by a clamping device, with magnetic clamping, preferably directly on the shield material, which may have an opening for contact of the magnetic clamping elements. By means of spacer 60, a sufficient distance between the glasses and the shield is achieved for the eyepieces and lenses of the magnifying glasses. FIG. 5b shows the clamping mechanism in detail.

FIG. 6a shows a clamping device for lamps and/or cameras that can be attached directly to the shield. This allows the optical element, camera, lamp, sensor, etc. to be attached directly to the shield 30, and if necessary several of them at the same time. The mass of the camera and/or lamp including battery is between 5 and 40 grams, preferably between 10 and 30 grams, in the case of lightweight construction. FIG. 6b shows an attachment with this magnetic clamping device on top of a sign according to the invention.

Common to the various embodiments is the solution to the task of attaching any necessary accessories such as lightweight LED lights in front of the protective shield, in particular to avoid disturbing reflections, absorptions and heating of the protective shield.

The proposed solution comprises at least a first clamping device which on the one hand carries the accessory, for example the LED light, and a second counter-clamping device which together with the first clamping device generates a clamping force or holding force, preferably by magnetic action or by other forces acting in a mechanically comparable manner. In a preferred embodiment, an LED light or a camera comprises an alignable element and a first clamping element to be able to adjust and fix the LED light or a camera in its alignment relative to the protective shield. The preferred variant comprises a mechanically stable spacer with a second clamping element on the one distal side and a third clamping element on the proximal side facing the head frame/glasses frame, and the head frame/glasses frame comprises a fourth clamping element that generates a clamping force with the third clamping element with which the spacer is stably fixed relative to the support frame/glasses frame. Through this mechanical chain of clamping elements, firstly the protective shield is fixed between the first and second clamping elements, and furthermore this group of elements or devices is fixed to the holding frame/glasses frame. In addition, further clamping devices can be attached which also contribute to stabilizing the protective shield relative to the wearer's head.

DESCRIPTION OF PREFERRED EMBODIMENTS

In the following description of preferred embodiments of the present invention, identical reference signs denote identical or comparable components.

FIG. 1: State of the art: eye protection at the top of the surgical mask.

Figure 1A:
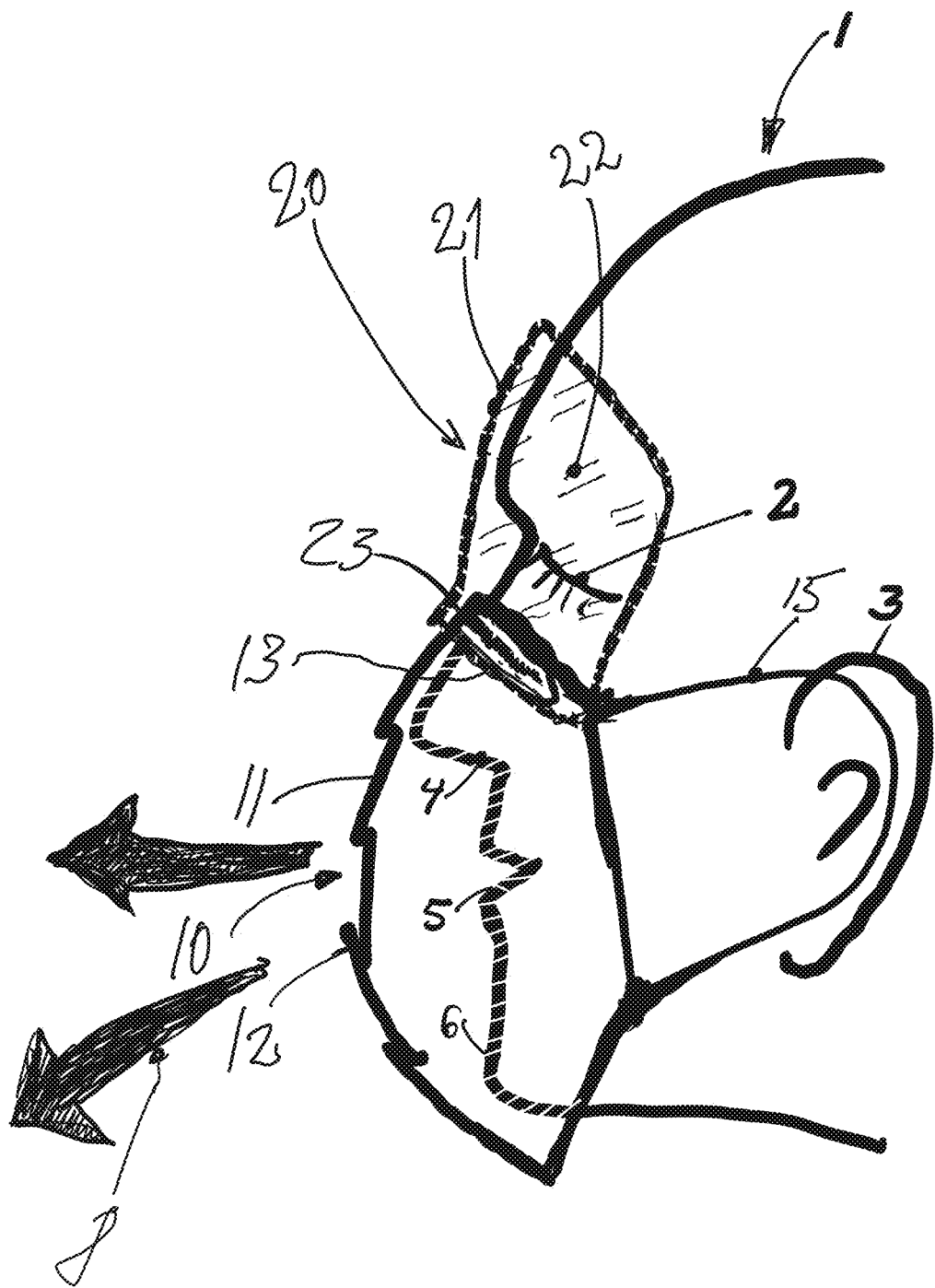
FIG. 1a illustrates a prior art protective shield, according to an example embodiment.
Figure 1B:
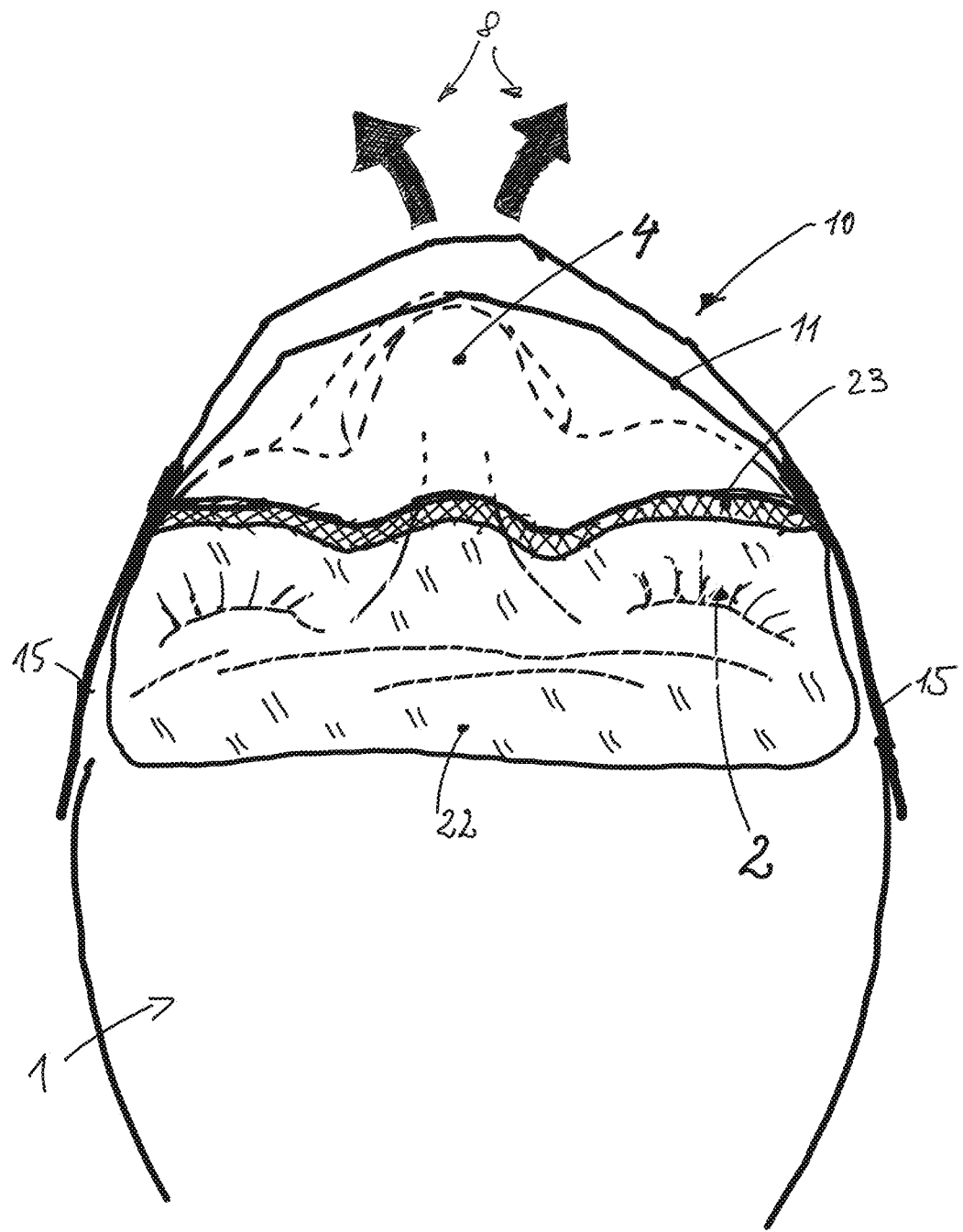
FIG. 1b illustrates a top view of the prior art protective shield of FIG. 1a, according to an example embodiment.

FIG. 1a shows a schematic sketch of the side view of the head 1 of the wearer of the mouth-nose guard 10 with eyes 2, ears 3, nose 4, mouth 5 and chin 6. Mouth 5 and nose 4 are covered by a mouth-nose guard 10 acting more or less well as a filter. FIG. 1b. shows the arrangement from above. The material 11 is usually a fabric, preferably multilayered. Individual adaptation to the shape of the face is usually provided by fold structures 12, and there are many variants on the market in this respect, including those with a stable frame and with adaptable deformation elements. The known mouth-nose guard optionally has a connection area at the top to an eye shield 20, connected via connecting area 23. The protection of the eye shield 20 can partially cover the forehead and have a curvature 22 that follows the forehead. The material 21 is transparent at least in the eye area 2, circumferential non-transparent edges are possible, as well as further connecting areas for connection to head hoods, etc. Despite all these details, this arrangement has serious hygienic shortcomings, because it splashes unhindered on the mouthguard. Likewise, the wearer can touch this mouthguard unhindered, which often happens unknowingly. This happens because the mouthguard is not covered but openly accessible. Since the mouthguard is usually moist, it represents a breeding ground for germs. In addition, in the event of rapid air movements, for example when coughing or speaking, the mouth-nose guard 10 can emit aerosol contamination that can affect the patient. This risk of contamination must be prevented in particular. Thus, the mask 10 basically has a filter area 11 that can be contaminated by splashes and/or aerosols. The pull strap or elastic band 15 holds the mouth-nose guard 10 to the ears 3, the protection can rest on the front of the nose 4, wherein, again, there is a risk of contamination that can be transferred to the patient. The protective shield 20 optionally added above is quite close-fitting or also inclined forward, with seam 23. The material 21 of the eye protection 20 is usually colorless transparent. Characteristic for the group of these variants is that the breathing air can flow to the patient during exhalation. This also applies to the variants with lateral blow-out valves in particular, as they are used especially for protection against chemicals, these have a high protection class for the wearer but a poor protective effect for the opposite or the patient. This is because contaminated material and possibly liquid collects at the blow-off valve due to condensation and is then ejected as drops or aerosols.

FIG. 1a shows the prior art with a textile mouth-nose guard 10 and an eye shield 20 coupled to the top, but leaving the mouth-nose area exposed. The consequence is the danger of contaminating the filter area 11, 12, by touch and by splashes. The nose 4 is covered by the filter element or by textile or by other materials, the mouth 5 as well and in the vast majority of embodiments also the chin 6. The disadvantages are described above. The air 8 flowing out through the filter can reach the patient directly and contaminate him by aerosol.

FIG. 1b shows the same arrangement systematically from above. One can see the joint 23 where the eye shield is coupled to the mouth-nose guard 10. The filter fabric 11 lies openly unprotected. The eyes 2 are covered by the splash guard. Both together are held by the rubber bands 15, which hold preferably to the ears.

The unhindered transfer of contaminated air or droplets between the wearer and the patient poses an unreasonable risk to the patient in many FFP3 masks used by dentists. Most of the time, this major risk is not discussed, but for the containment of spreading infectious diseases, it is very important to at least reduce the contamination load for both parties involved, the mask wearer and the patient on both sides.

FIG. 2: Protective shield clamped to the side of the mouth-nose guard

Figure 2A:
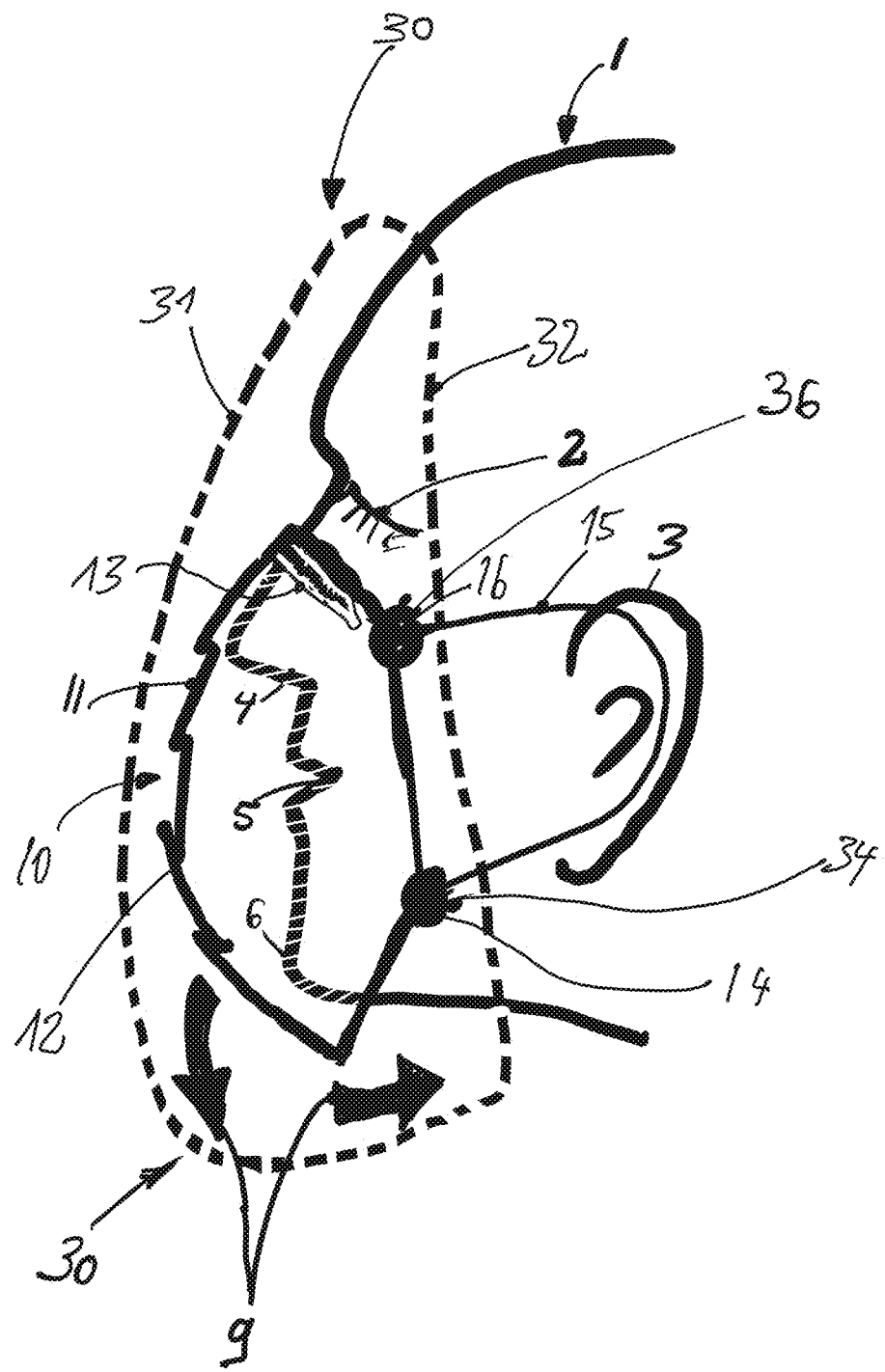
FIG. 2a illustrates a protective shield, according to an example embodiment.
Figure 2B:
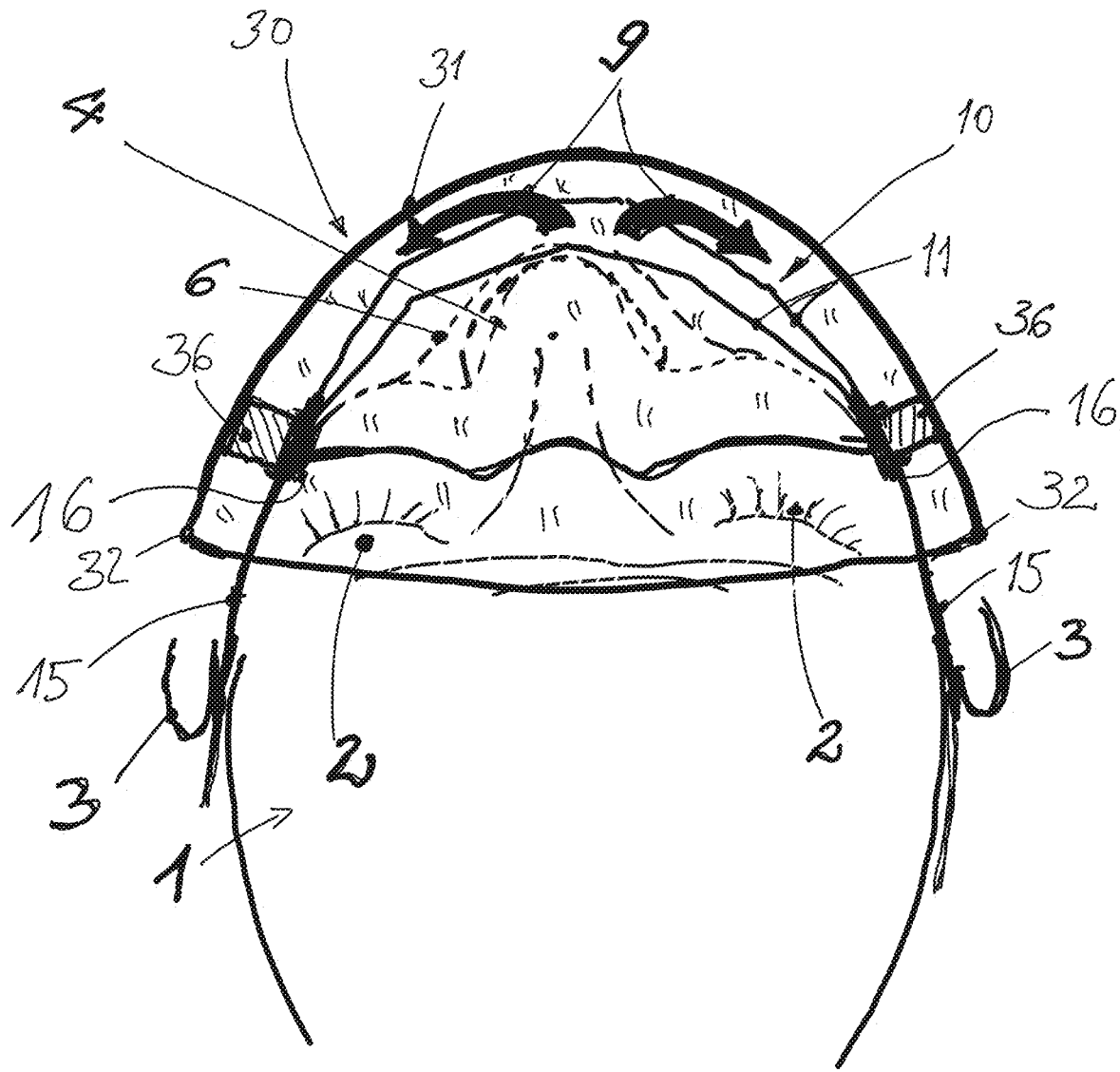
FIG. 2b illustrates a top view of the protective shield of FIG. 2a, according to an example embodiment.

FIG. 2a shows a side view of the head of the wearer 1 with the mouth-nose guard 10 attached and with the protective shield 30 attached to it. FIG. 2b shows the constellation from above. The protective shield 30 is preferably a visor extending from under the chin to above the eyebrows. The material is waterproof and transparent at least in the field of view of the eyes, preferably also in the other areas. It may be a thin film of polycarbonate or of acetate or of some other material that is sufficiently optically transparent not to interfere with the wearer's view. The film may also be coated, particularly to reduce reflections and to prevent fogging caused by condensing moisture from the breathing air. The protective shield 30 with its coupling devices 34, 36 is mechanically coupled to the mouth-nose guard 10 directly via coupling elements 14 and 16 or indirectly via spacer elements so that its relative position and spatial orientation relative to the head of the wearer is largely fixed. The necessary holding force for the mouth-nose guard 10 is thus increased, depending on the weight and design of the mouth-nose guard and the protective shield, and in particular also on the distance of the shield from the face. If necessary, further holding points can be introduced between the protective shield and the head, which are not shown here in FIGS. 2a and 2b. Shown schematically is the holding of the mouth-nose guard 10 by partially elastic loops 15, which are guided around the ears 3. The attachment point of the holding device 15 can coincide with the coupling points 14, 16 for the shield or be designed separately. It is characteristic that the entire mouth-nose area and thus also the mouth-nose guard 10 is covered. Contamination of the filter element 11 is thus prevented. In addition, the flow of the outflowing breathing air 9 is deflected, and in particular, in the example of use by a dentist, it no longer hits the patient directly when exhaling or coughing. Optionally, the mouth-nose guard carries an adaptation element 17 for sealing adaptation, in particular to the individual contour in the nose area, in order to prevent the moist breathing air from escaping there in the direction of the eyes, in particular also to prevent fogging of glasses lenses and self-contamination of the eyes. This simplified arrangement avoids touching of the mouth-nose mask and the face. In addition, splashes coming from the patient are intercepted and the transfer of contaminated exhaled air directly to the patient during coughing or when the exhalation valves open is prevented.

FIG. 2a shows a preferred embodiment of the protective shield 30 with a shell shape drawn backwards towards the neck at the chin, which may be necessary to prevent splash contamination from below, e.g. for dental use by the dentist. Conversely, this shape of the splash guard 30 also deflects the outflowing respiratory air schematically following the arrows 9 and does not flow directly to the patient. This protects the patient from contamination. Coupling elements 14, 16 on the mask correspond with spacing elements 34, 36 on the shield 30 to provide a spacing of the shield from the cheeks at the side of the face. The mask 10, to which the shield 30 is attached, is fastened to the ears 3 or to the head 1 of the wearer. Preferably with partially elastic band elements 15. FIG. 2b shows the shield 30 attached to the mouth-nose guard 10 from above, analogous to FIG. 1a. The mouth-nose mask 10 itself is fastened to the head with sufficiently stable tension straps, e.g. leading backwards above and below the ears, preferably also with partially elastic tension straps with surface adhesion, which can be easily fixed to the back of the head. The attachment of the straps 15 to the ears 3 is only one of the possibilities and in many cases permanently not sufficiently stable, but for very light arrangements without further attachment elements at the shield 30 quite functional. The protective shield 30 may have a shell-shaped form as shown, but it may also be shaped like the lateral surface of a cylinder (see FIGS. 4a and 4b) or include beveled flat areas.

Figure 2C:
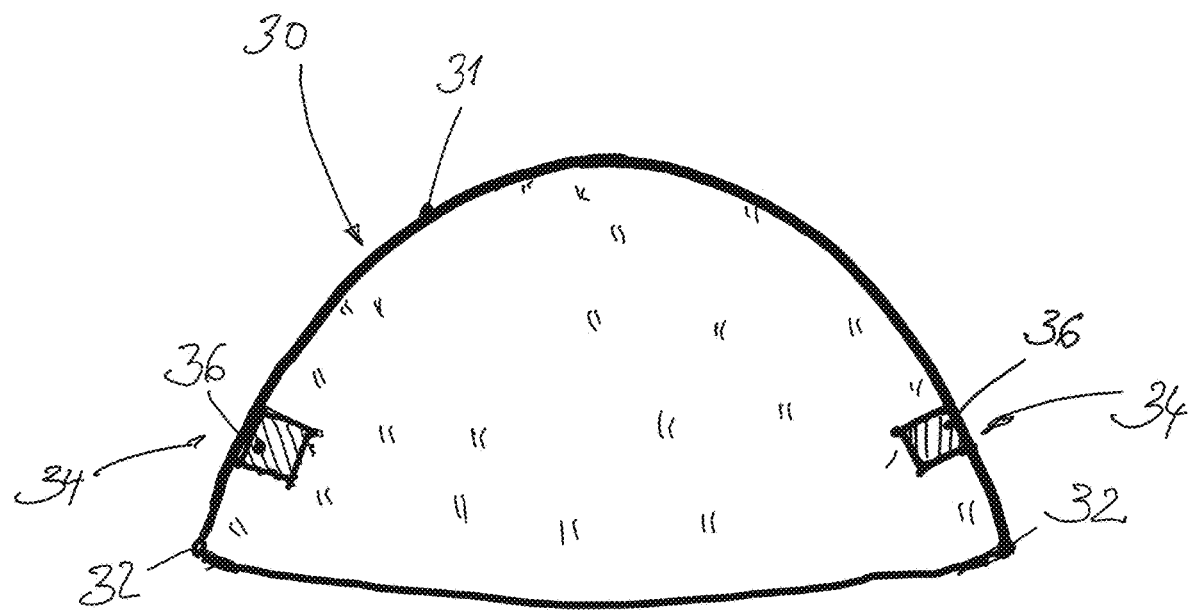
FIG. 2c illustrates the protective shield of FIG. 2a with coupling elements, according to an example embodiment.

FIG. 2c shows an embodiment of the protective shield 30 with coupling elements 34, 36, which are used for coupling to the coupling elements 14,16 on the mouth-nose guard. Due to the ellipsoidal curvature in two spatial directions, the shield in this embodiment has a comparatively spatially stable shape of its own even without the coupling. For an alternative embodiment of the shield 30 without a shell shape, the curvature requires attachment in at least two locations, such as three locations on a glasses frame, front and left and right sides, or on the mask. see FIG. 4a and FIG. 5a.

FIG. 3: Fastening the protective shield with central clamping piece

Figure 3A:
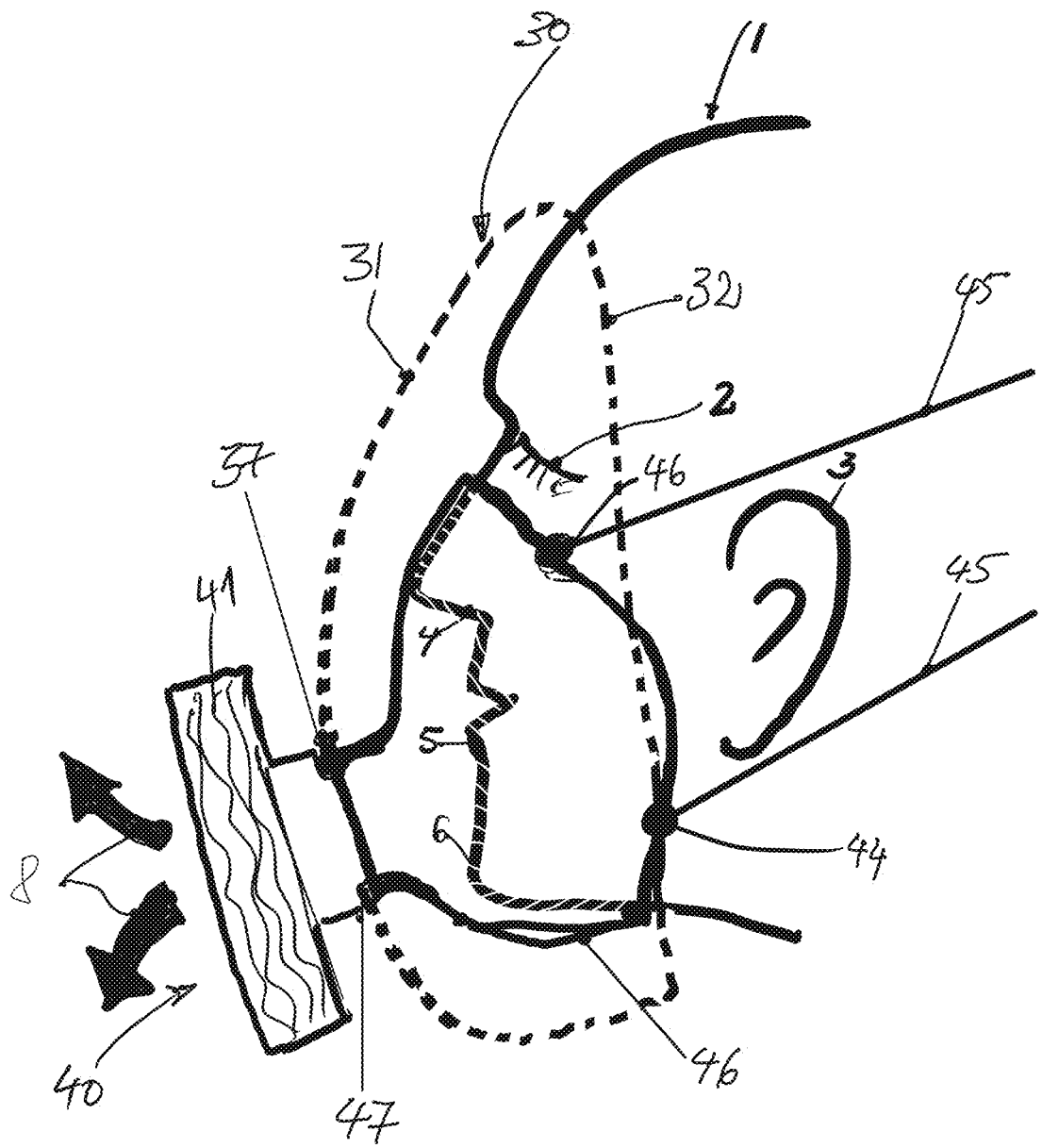
FIG. 3a illustrates another protective shield, according to an example embodiment.
Figure 3B:
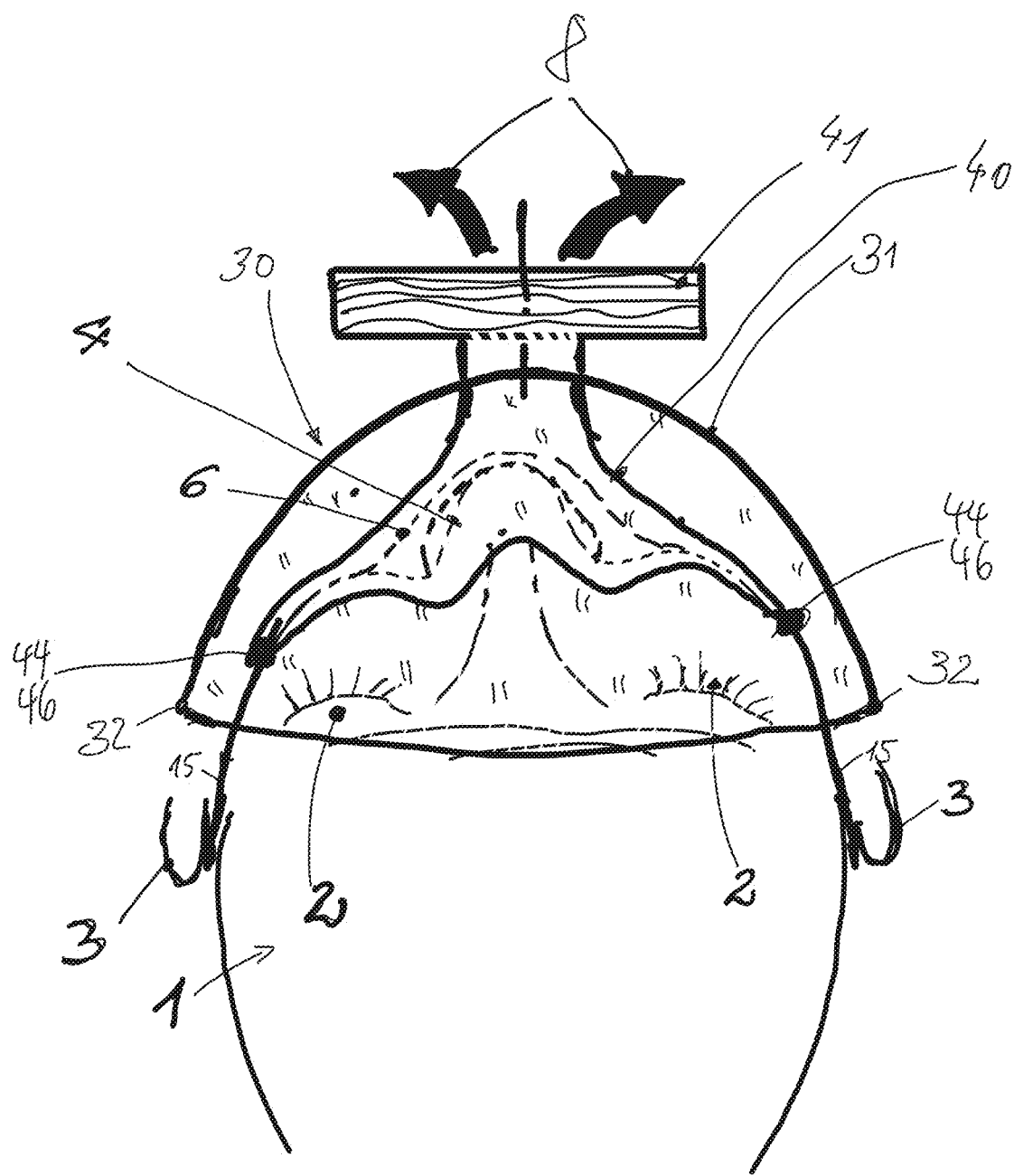
FIG. 3b illustrates a top view of the protective shield of FIG. 3a, according to an example embodiment.
Figure 3C:
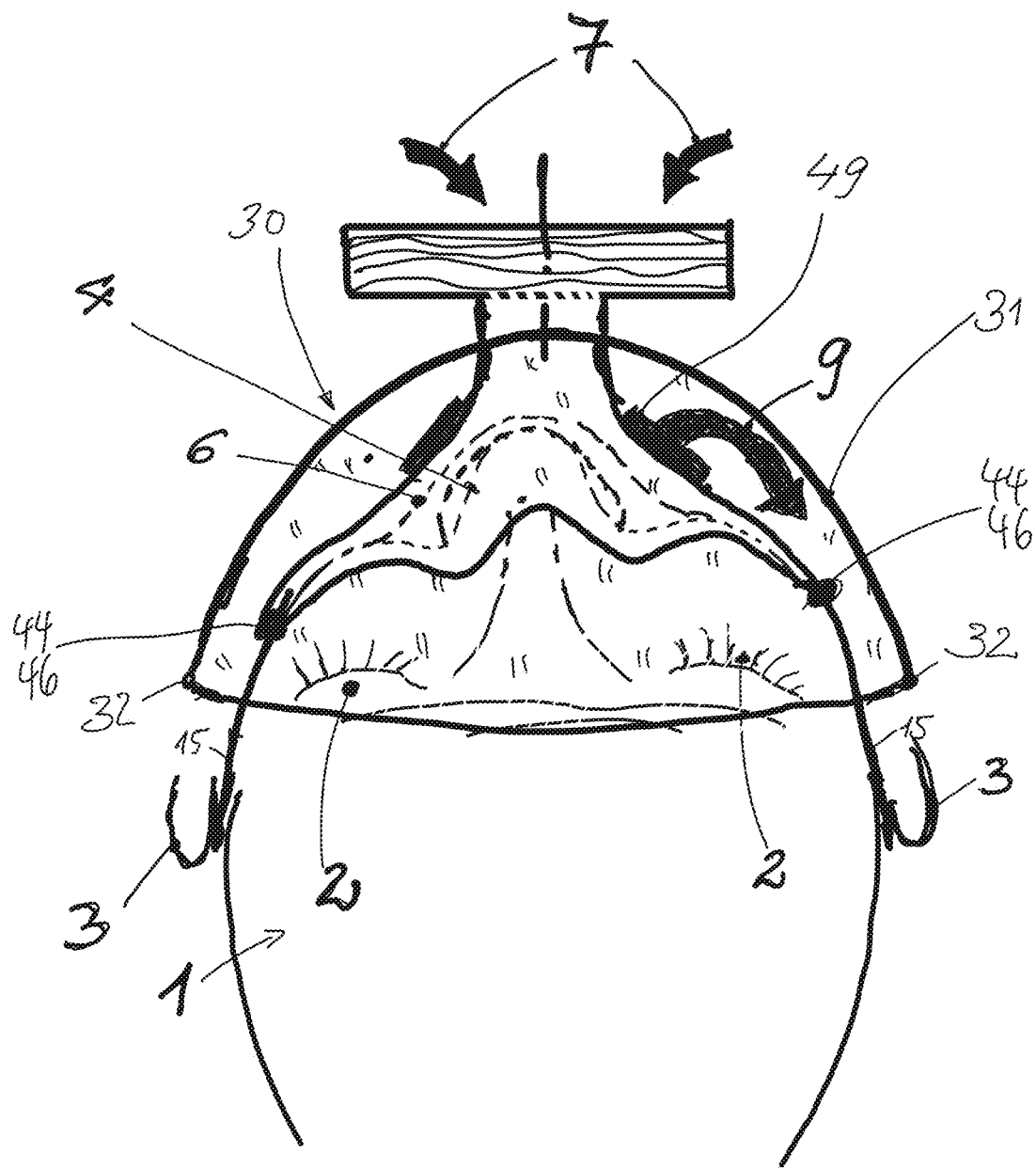
FIG. 3c illustrates a top view of the protective shield of FIG. 3a, according to an example embodiment.

FIG. 3a shows a further embodiment in simplified schematic representation in side view. FIGS. 3b and 3c show the constellation in top view. The protective shield 30 or visor, respectively, is here attached to a central coupling element 47 on the breathing mask 40, which is mechanically stable at least in this area. The mouth-nose guard 40 here has more the form of a respiratory mask with preferably replaceable filter element 41, which can preferably be reached from the outside for filter replacement, preferably without having to remove the mask.

This mouth-nose guard 40 comprises an individually adaptable sealing area 46, which fits circumferentially around the mouth and nose as completely and as tightly as required by the protection classes, e.g. for a tightness of at least 95% for FFP3 masks. The sealing area is designed in terms of material selection and material thickness so that it can fit against the wearer's face without undue stress on the wearer in order to achieve sufficient tightness. For this purpose, the tension elements 15 must provide sufficient force, although this can usually no longer be achieved by ear fastening. The shape of the mask 40 may have been determined on the basis of individual 3D data of the head 1 of the wearer, thus having an individual fit. In particular, the sealing area 46 also extends over the nose 4 and under the eyes 2. Flexible elements may be attached at points of low elasticity, for example foam elements or sealing lips. The material of the protective shield is sufficiently stable, at least in the coupling area 37, to transmit a holding force to the protective shield 30. Preferably, there is an aperture 37 in the shield 30, with a diameter of preferably at least 10 mm, particularly preferably at least 20 mm. An adapter piece leads through this aperture 37 of the shield 30, which can create a clamping effect and sealing effect between the mask 40 and the shield 30. In the vicinity of the lead-through or directly as part of the lead-through, preferably mechanical keying elements are provided which create a spatial orientation between mask 40 and shield 30. Alternatively, in the vicinity of the opening 37, the shield 30 is held and fixed in its orientation solely by the frictional force on the clamping element 47. Distally beyond the shield 30, the filter element 41 can be connected to the breathing air path of the mask 40. Preferably, different filter variants are available for this purpose, which can be coupled to the adapter 47. The mask 40 can also be used without the protective shield 30, but then with increased bidirectional contamination risk. This mask 40 also has at least two fastening elements 44, 46 which correspond to coupling elements 34, 36 on the shield and which can be reversibly connected and disconnected again.

In particular embodiments, the connection between the shield 30 and the mask 40 or mouth-nose guard 10 is not reversible but permanent.

In another embodiment, fastening elements that are located laterally (see FIGS. 2a and 2b) are combined with fastening elements that are located centrally at the front (see FIGS. 3a, 3b and 3c). This results in increased stability and load capacity of the coupling of the shield 30.

In addition, the protective shield can also be supported in the upper head area, e.g. by coupling it to glasses or by means of a forehead support. This serves in particular to stabilize the upper shield area in the event that a lamp, camera or other accessories are to be clamped to the shield 30.

FIG. 3a shows another way of attaching the shield 30, now to a more mechanically stable breathing mask 40 with a flanged replaceable filter element 41. The mouth-nose mask portion 46 is preferably shaped to fit individually. The holding force on the head positions the mask securely around the mouth and nose to achieve the required tightness. Air exiting through the filter 41 can reach the patient, but is filtered. Attachment to the head is via the retaining points 44.

FIGS. 3b and 3c show the mask 40 from above and the shield 30 attached to the mask 40. Here again with a curvature. One can see the guidance of the inhaled air through an aperture 37 into the mouth and nose, and out through the filter again if required. Next to this is a relief valve 49, see FIG. 3c, through which air can escape when coughing, etc. This escaping air flow 9 is deflected by the shield 30 and cannot reach the patient directly. However, there may also be valves or additional filter paths for exhalation, in which case the exhaled air is deflected by the shield similar to FIG. 2b.

Figure 4A:
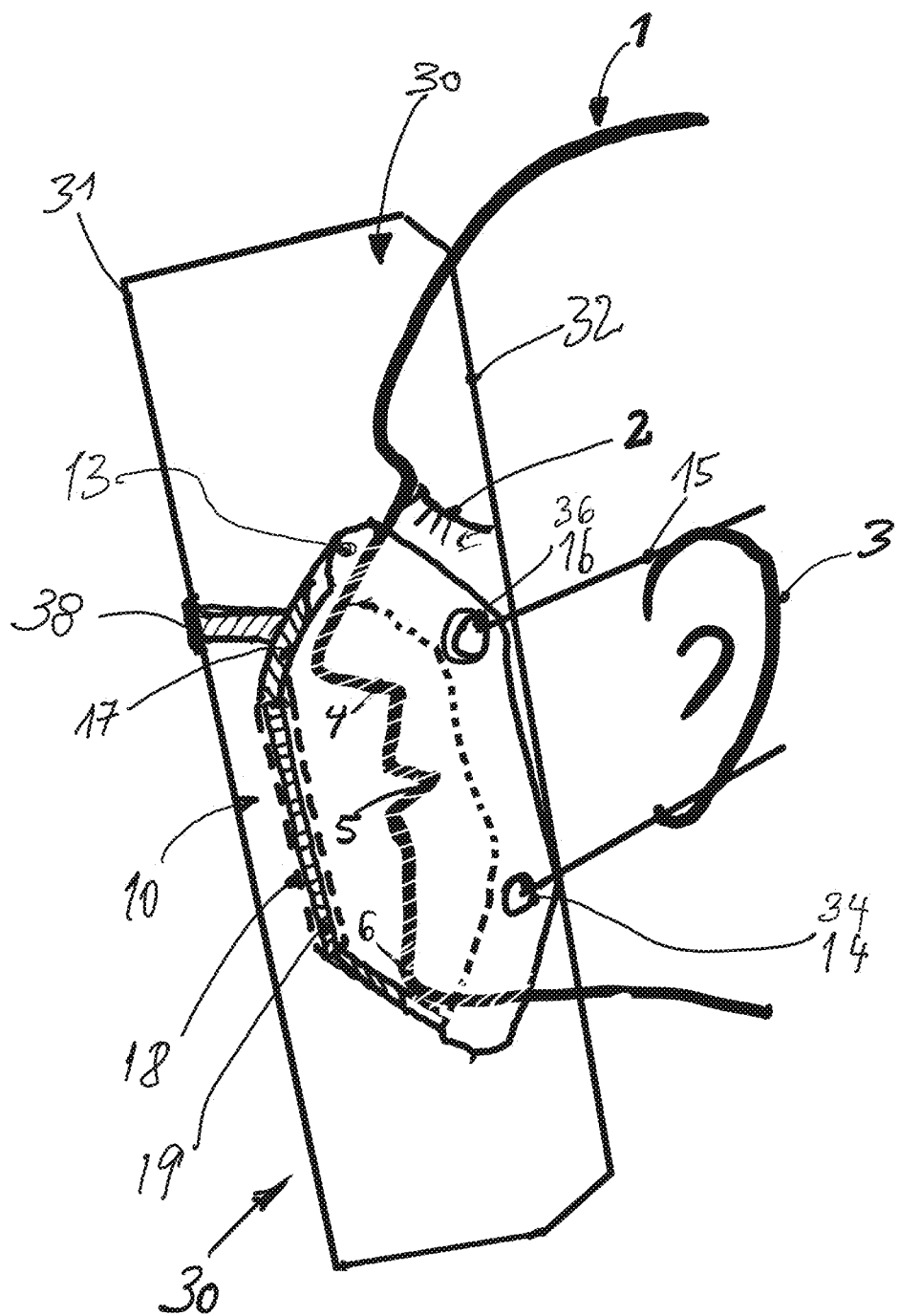
FIG. 4a illustrates another protective shield with a mouth-nose guard, according to an example embodiment.
Figure 4B:
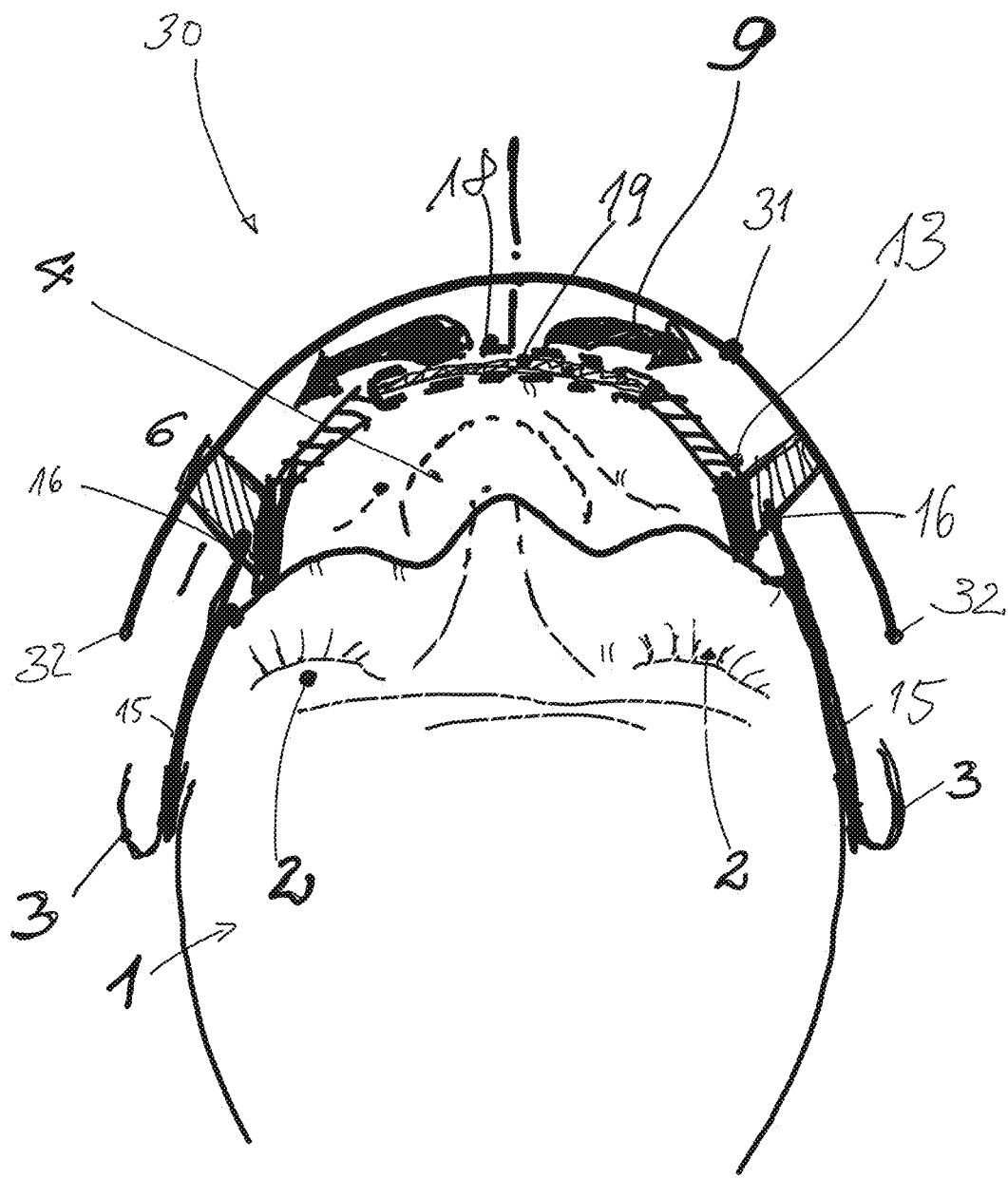
FIG. 4b illustrates a top view of the protective shield of FIG. 4a, according to an example embodiment.

FIG. 4: Shield attached to mouth-nose guard with internal replaceable filter FIG. 4a shows a side view of another embodiment of the shield in combination with another embodiment of a mouth-nose guard 10. FIG. 4b shows the constellation and the air path from above. Here, the shield 30 is predominantly curved in only one spatial direction, i.e., it is predominantly in the form of a section of a lateral surface of a cylinder. The cylindrical curvature of the shield results here from the interaction of several holding points 34 laterally above, 36 laterally below and 38 centrally in front. These correspond to the coupling elements 14, 16 on the mask 10. The optional spacers on the right, left and front create the distance of the shield from the mask and face. The airway does not pass through the shield here, and the aperture 37 in the shield is not present. The mask includes replaceable filters 19 and a permeable filter cover 18. The sealing rim may be circumferential with sealing lip or foam elements, or may be customizable. The filter 18, 19 is located on the side of the mouth relative to the shield. Thus, both the flow of the inhaled air is guided by the shield and the flow of the air 9 exiting through these filter elements 19 and the cover 18. The coupling of the shield 30 takes place via coupling elements which are preferably located in the mechanically more stable area of the mask 10, which can have the function of a predominantly dimensionally stable three-dimensional frame 13, which also supports the cover 18 of the filter element 19. Here, too, different filter elements can be used depending on the requirements. This frame is pulled backward against the face by the strap attachment 15, providing stability to the mask relative to the head. The shield 30 is optionally shell-shaped or cylindrical in shape and is attached to the mask or to the mouth-nose guard 10, respectively.

FIG. 5: Shield clamped to frame and lamp

Figure 5A:
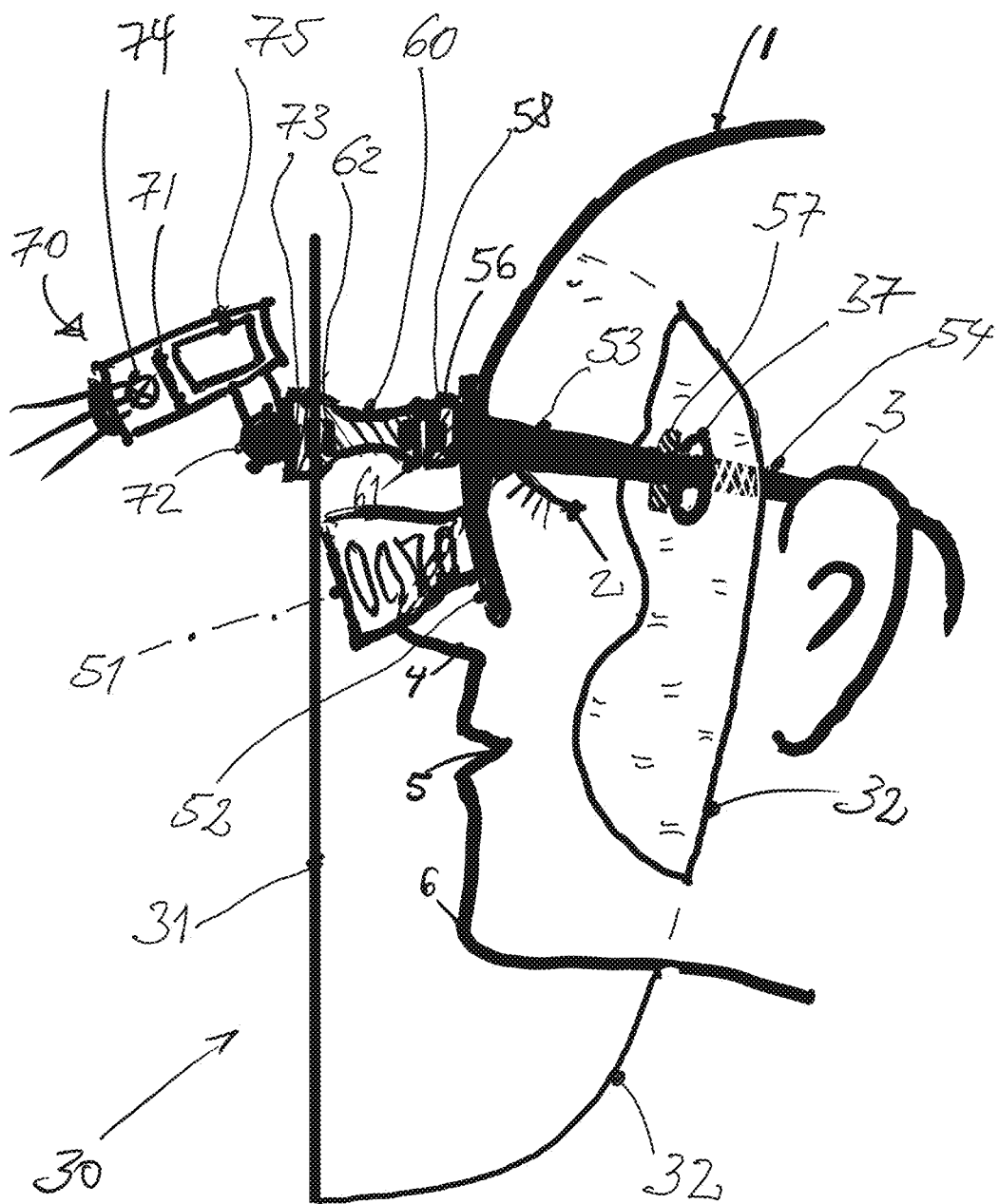
FIG. 5a illustrates another protective shield, according to an example embodiment.

FIG. 5a shows a schematically sketched protective shield 30 with predominantly sole attachment not to the mouth-nose guard but to a glasses frame 52, e.g. a pair of magnifying glasses, preferably in the area between the eyebrows. In this embodiment, the magnifying optics 51 are attached to the glasses lenses or to the frame 52. The transparent protective shield 30 made of material 31 has a lateral edge 32 and may have rectangular or also rounded contours, have beveled flat areas and have cylindrical or ellipsoidal curvatures. The shield is attached for stabilization firstly centrally above the nose to the glasses temple 53 and laterally to the ear temples, preferably by inserting the glasses temples 53 through holes 37 in the shield 30, or by fastening elements 57 on the glasses temple holding the shield at lateral attachment points 37. The magnifying optics 51 require a forward spacing of the shield 30, which is preferably achieved by spacing elements 60. According to the invention, the fastening element clamping the shield 30 has at least a first clamping element 73 and a second clamping element 62. The spacer 60 is also self-holdingly fastened to the glasses frame 52, the clamping elements 58 and 61 cooperating here. Preferably, these are magnetically acting clamping elements. The length of the spacer 60 depends on the space requirement of the loupe optics 51.

Figure 5B:
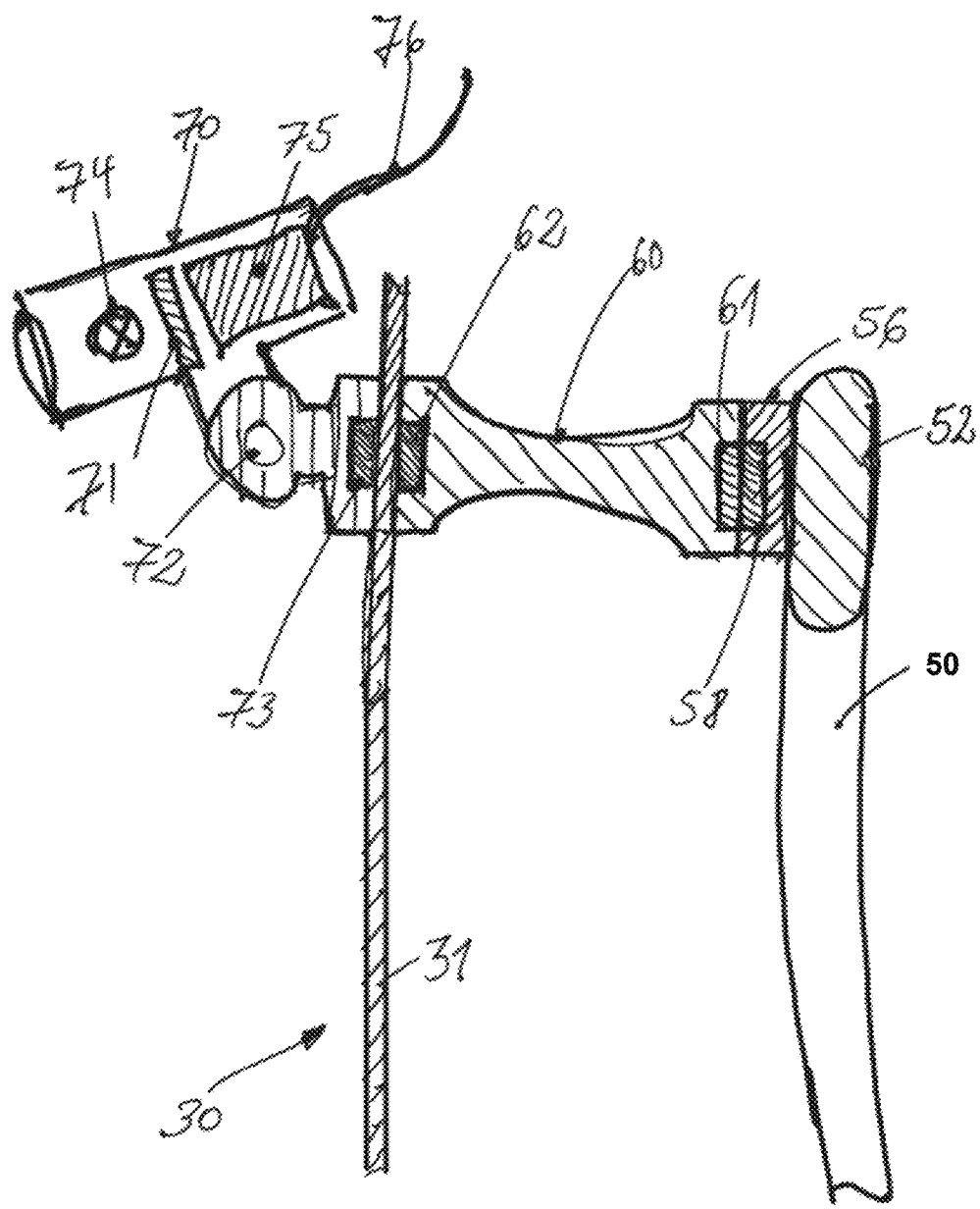
FIG. 5b illustrates another view of the protective shield of FIG. 5a, according to an example embodiment

FIG. 5b shows the arrangement of the elements on the magnetic clamp with spacer 60 in enlarged detail. The first clamping element 73 generates the clamping force together with the second clamping element 62. The spacer is held to the frame 52 of the glasses 50 via the clamping elements 61, 58.

Figure 5C:
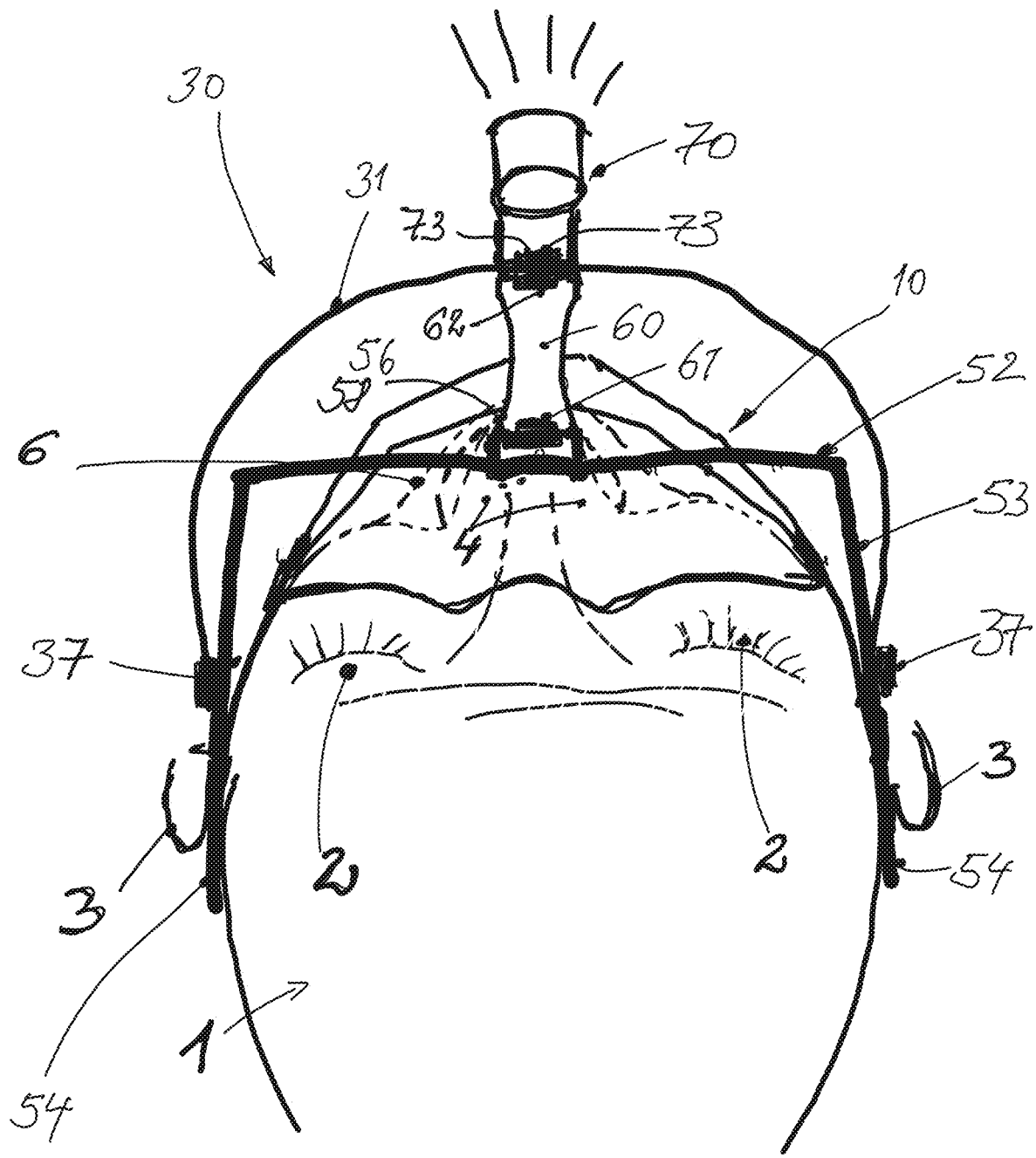
FIG. 5c illustrates a top view of the protective shield of FIG. 5a, according to an example embodiment.

FIG. 5c shows the constellation of the shield with magnifying glasses with lamp from above. Several auxiliary devices such as lamps 70 or cameras can also be arranged.

Figure 5D:
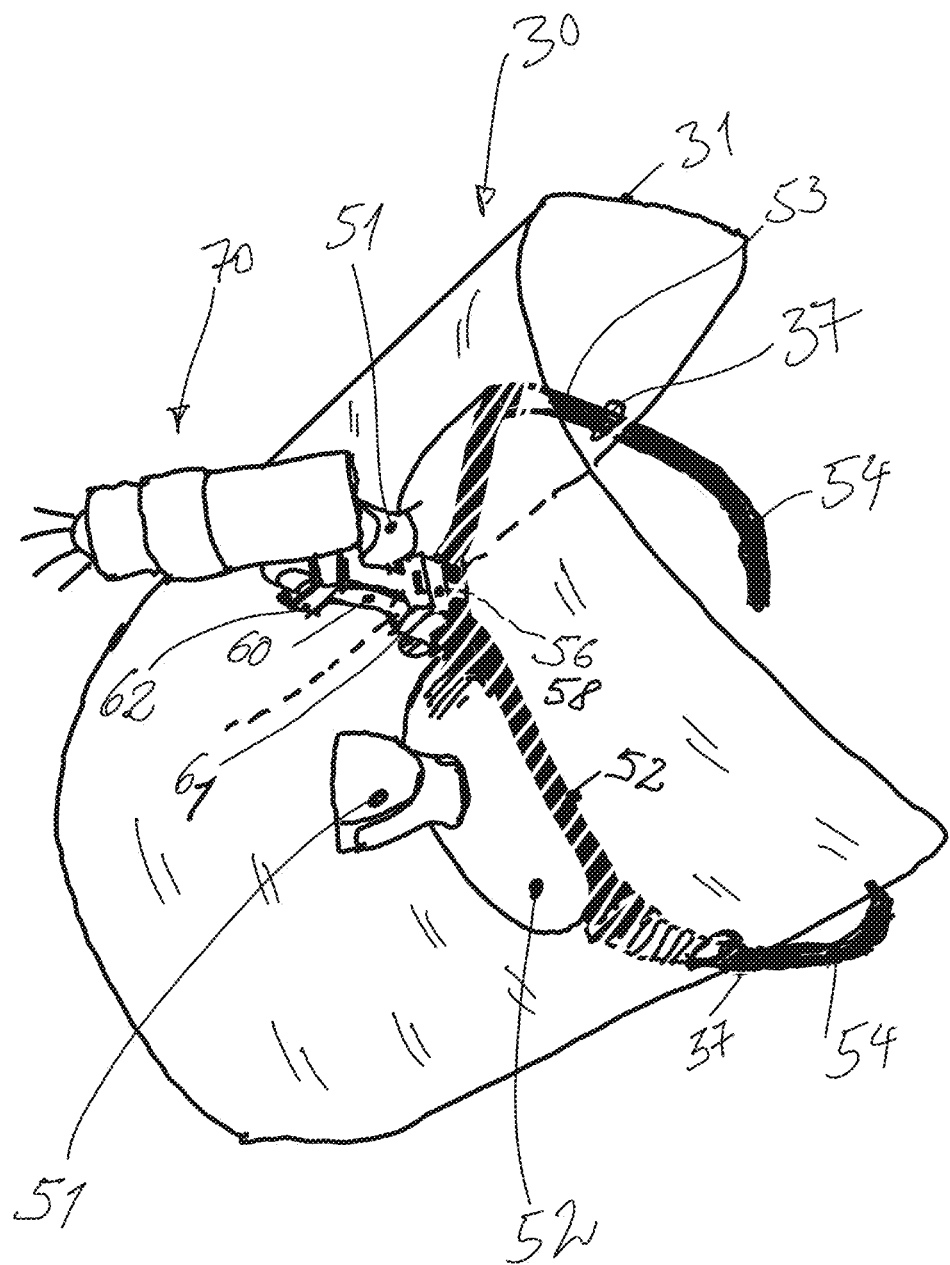
FIG. 5d illustrates a perspective view of the protective shield of FIG. 5a with attachment to magnifying glasses, according to an example embodiment

FIG. 5d shows a perspective view of a protective shield with attachment to magnifying glasses via clamping elements and spacer 60. Attachment of lamp 70 is optional, and the lamp can be replaced by an end piece (not shown). The protective shield 30 can also be attached to the mouth-nose guard (not shown).

Figure 5E:
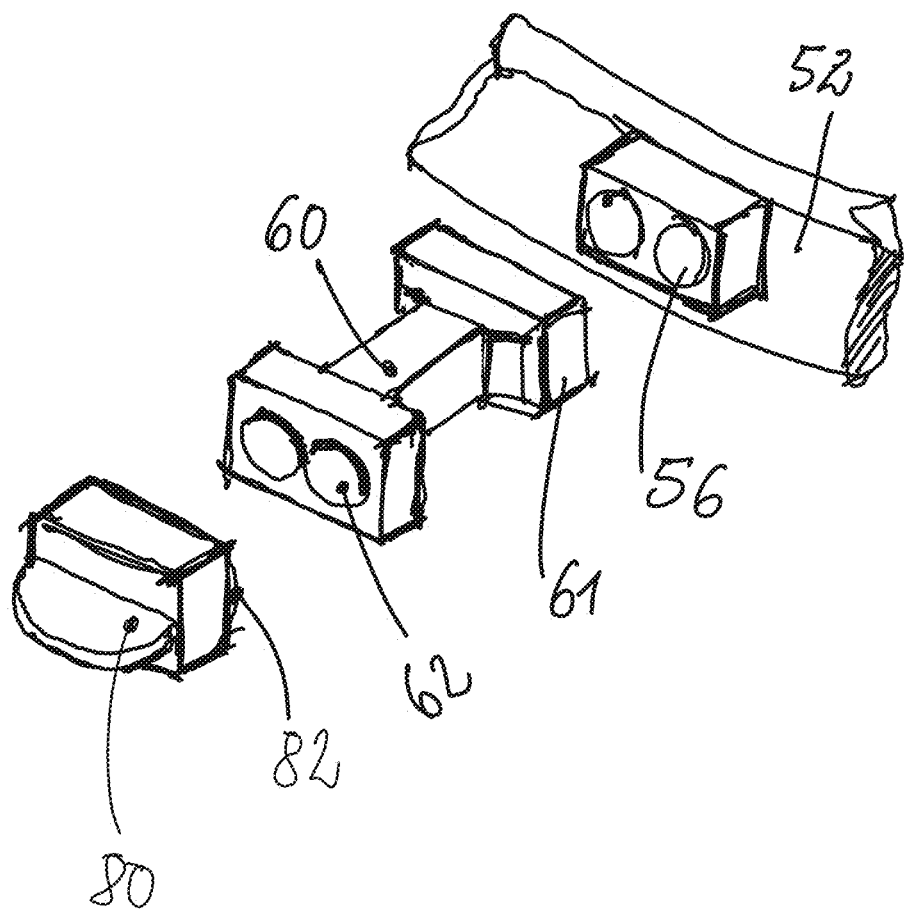
FIG. 5e illustrates a rotationally stable clamp attachment of the protective shield of FIG. 5a, according to an example embodiment.

FIG. 5e schematically shows a rotationally stable clamp attachment with two parallel magnetic clamping elements 58 in the clamp part 56 on the glasses side. Likewise, two magnetic clamping elements 62 in the spacer 60 and, in addition, an end cap 80 with clamping elements 82 to develop the clamping force for the shield 30. The end piece 80 can be replaced by a lamp or camera 70, with clamping elements 72, 73.

FIG. 6: Visor-magnet clamp for lamp/camera

Figure 6A:
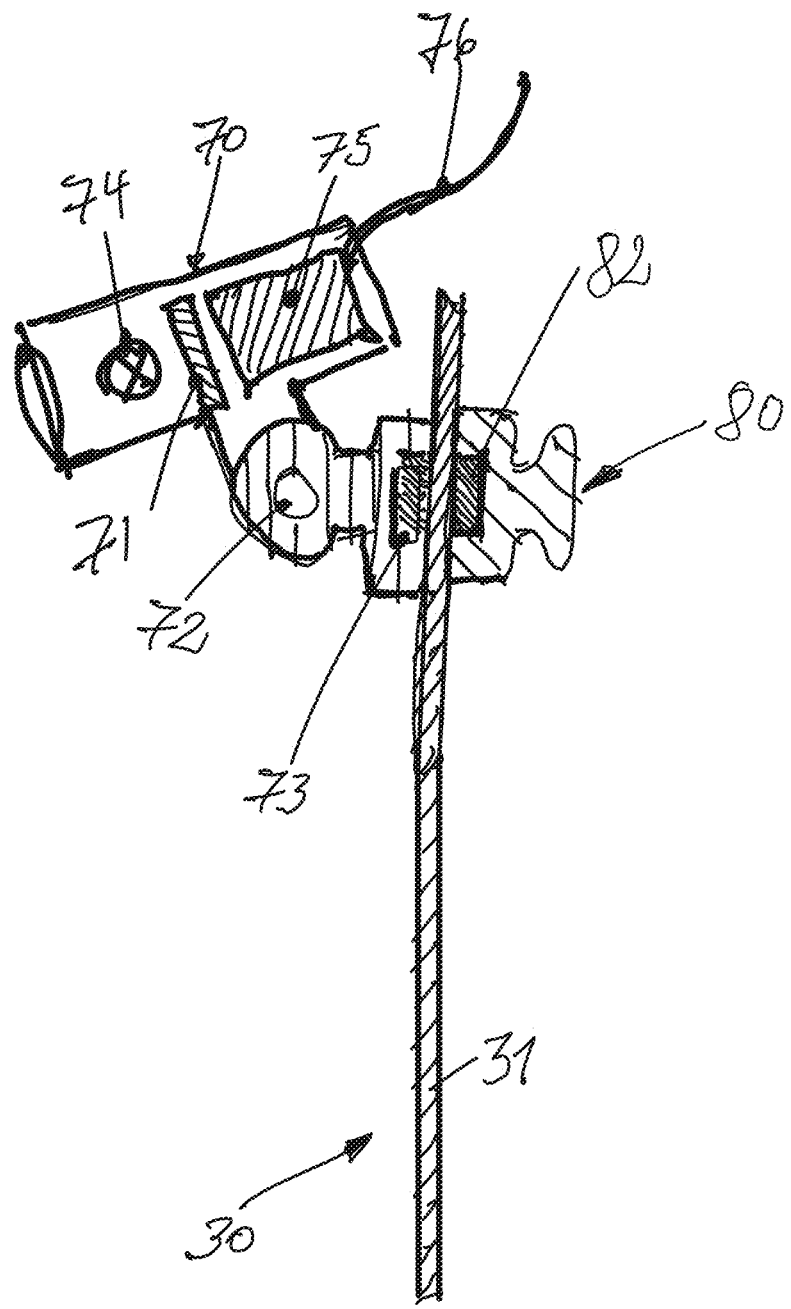
FIG. 6a illustrates a clamping device of a protective shield, according to an example embodiment.

FIG. 6a shows the clamping device with clamping cap 80 and clamping elements 82, 73 for clamping accessories such as lamps 70 or cameras. The clamping is done by means of static friction and/or mechanical keying directly to the shield 30. This allows the attachment of such accessories without the need for a glasses frame (compare FIG. 5a). The clamped equipment 70, in the example a micro LED battery light, is very light and can be removed if necessary. The weight is preferably between 5 and 50 grams, between 5 and 20 grams for embodiments without a battery with an external power source, and between 10 and 30 grams for embodiments with an integrated battery. In the embodiment shown without attachment to head frame or glasses, the accessory 70 is clamped via the first clamping element 72, 73 and a second clamping element 80, 82. The foil or pane 31 of the protective shield 30 is so thin or so widely perforated in the clamping area that the clamping effect is largely sufficient for stable fixation of the protective shield.

With modern magnetic elements 82 and 73, which can be identically oriented cylinder magnets, forces are achieved so that even foils up to 1 mm thick can be clamped. The smaller the gap filled by the shield between the clamping elements 82, 73, the greater the clamping force with the same magnets. Supporting and for better orientation of the shield 30, further orientation elements can be attached to the devices or elements 70, 60, 80, 50, which scramble with orientation elements on the protective shield.

Figure 6B:
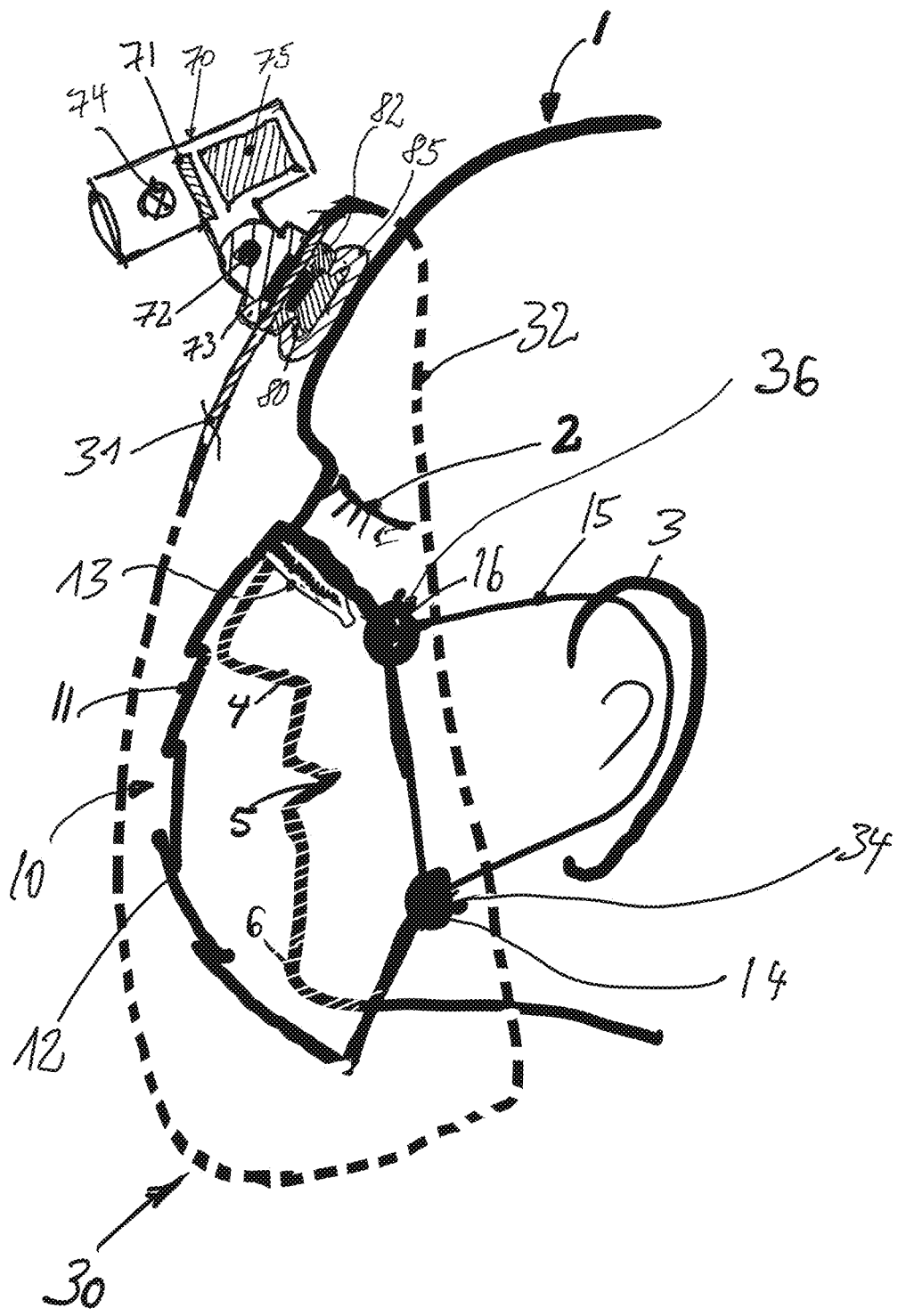
FIG. 6b illustrates the clamping device of FIG. 6a attached to an LED light, according to an example embodiment.

FIG. 6b shows an attachment of an LED light 70 to the shield 30 by means of the clamping device 72, 73, 82, 80. In addition, a support part 85 may be attached, in particular for supporting the lamp on the forehead.

FIG. 7: Shield with coupling elements for attachment to head-mounted device

Figure 7A:
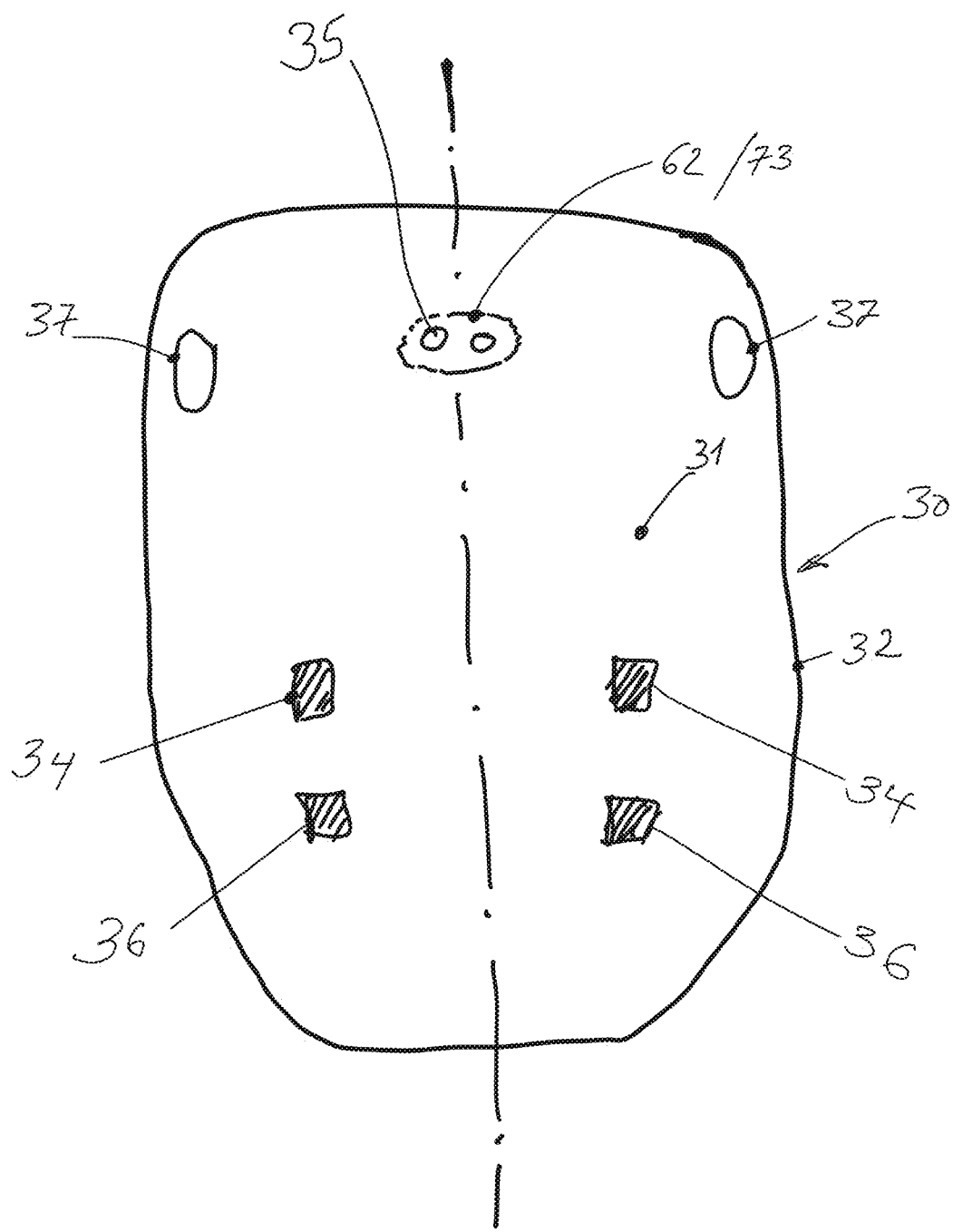
FIG. 7a illustrates another protective shield, according to an example embodiment.

FIG. 7a shows a protective shield 30 made of preferably transparent material 31 and with fastening elements 37 in the form of holes for the passage of glasses frames on the right and left and with further fastening elements 34, 36 for coupling to a mouth-nose guard or to a breathing mask equipped with coupling elements 14, 16. At the top center, one can see an opening for strongly clamping magnetic holders or other fastening elements for clamping the shield to a glasses frame with the aid of a spacer.

Figure 7B:
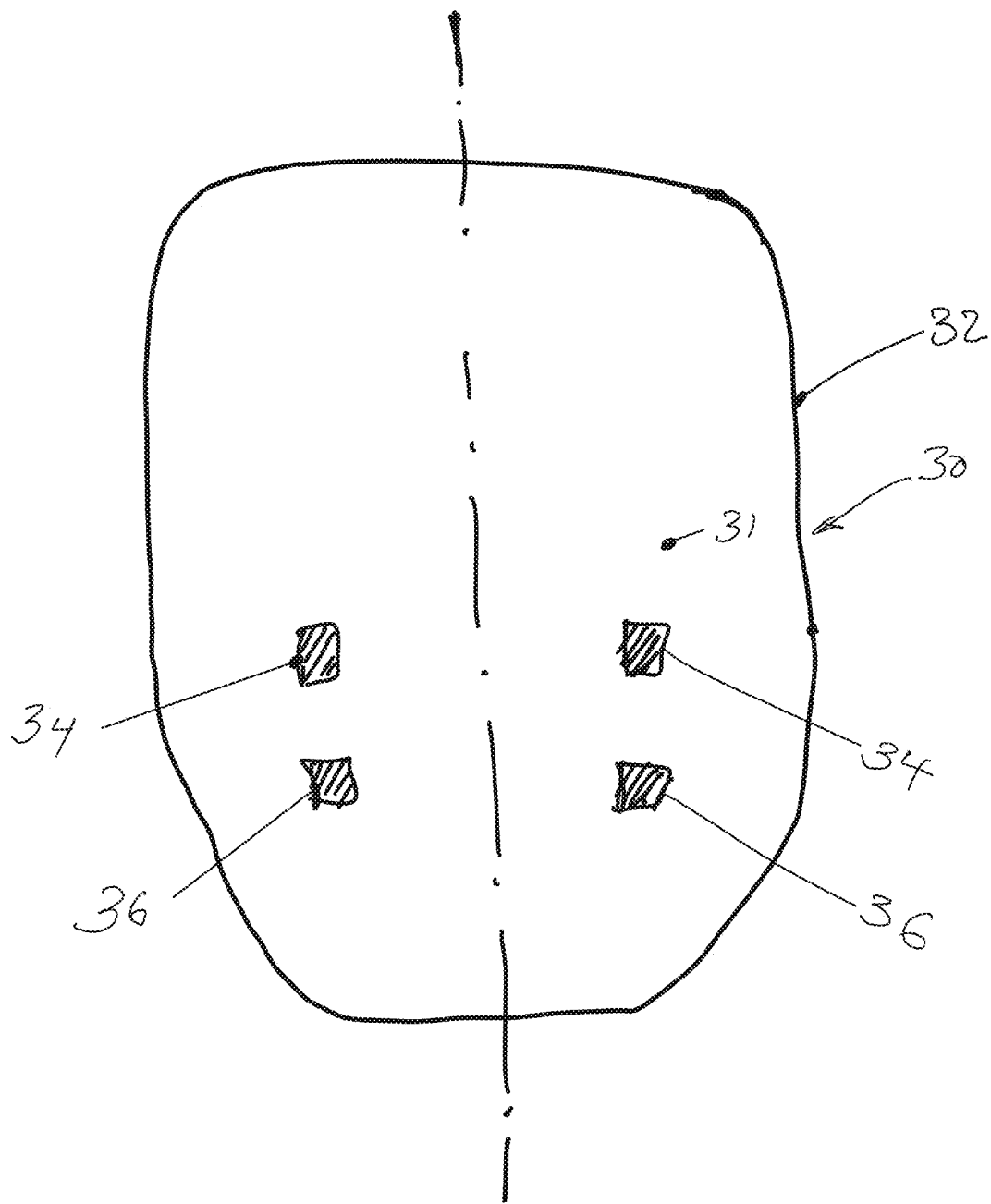
FIG. 7b illustrates an alternative example of the protective shield of FIG. 7a, according to an example embodiment.

FIG. 7b shows a preferred embodiment of the protective shield 30 without glasses attachment with attachment via the coupling elements 34, 36 to a mask (not shown) equipped with corresponding elements therefor. Plug-in elements, magnetic elements, Velcro elements and/or other coupling elements can be used for fastening.

Figure 7C:
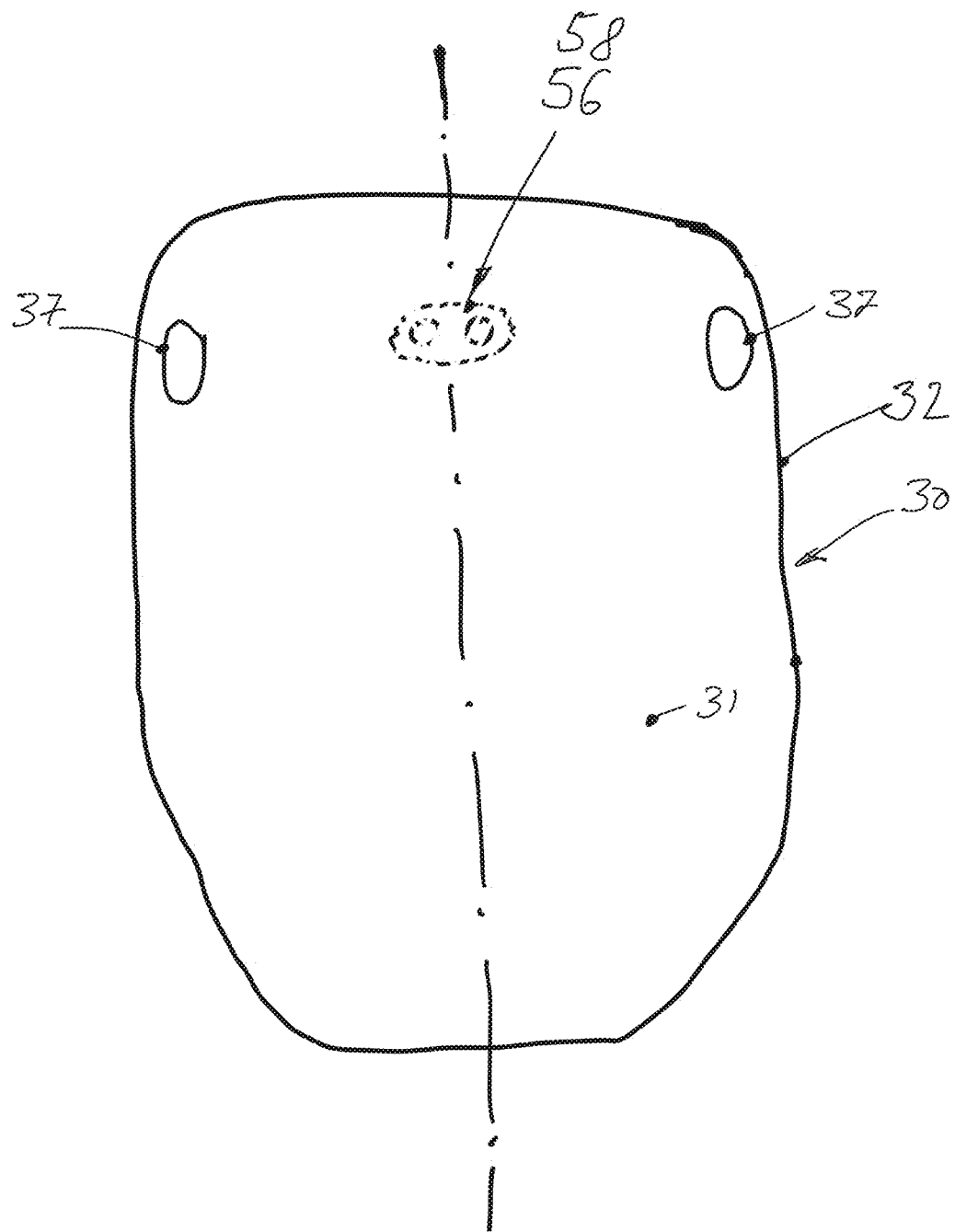
FIG. 7c illustrates an alternative example of the protective shield of FIG. 7a, according to an example embodiment.

FIG. 7c shows a shield 30 with coupling elements in the upper area prepared for coupling to glasses, without additional coupling to a mask. The particularly preferred embodiment comprises at least one fastening element 37 on the right and left side, respectively, for contact with the ear temples 53. Furthermore, at least one centrally arranged coupling element 56 for attaching a counter-clamping element 60 or 80 or 70, so that the pane of the protective shield is clamped at this point. Furthermore, holding elements may be attached which correspond to holding elements 57 on the glasses temples (not shown. See FIG. 5a).

The mechanical stability of the shield 30 at the clamping point is achieved by an at least one-dimensional curvature. Depending on the application, one-dimensional curved shields like in FIG. 4 and FIG. 5 or two-dimensional curved shields like in FIGS. 2 and 3 as well as FIG. 6b are suitable.

FIG. 8: Shield for protection against laser radiation

Figure 8A:
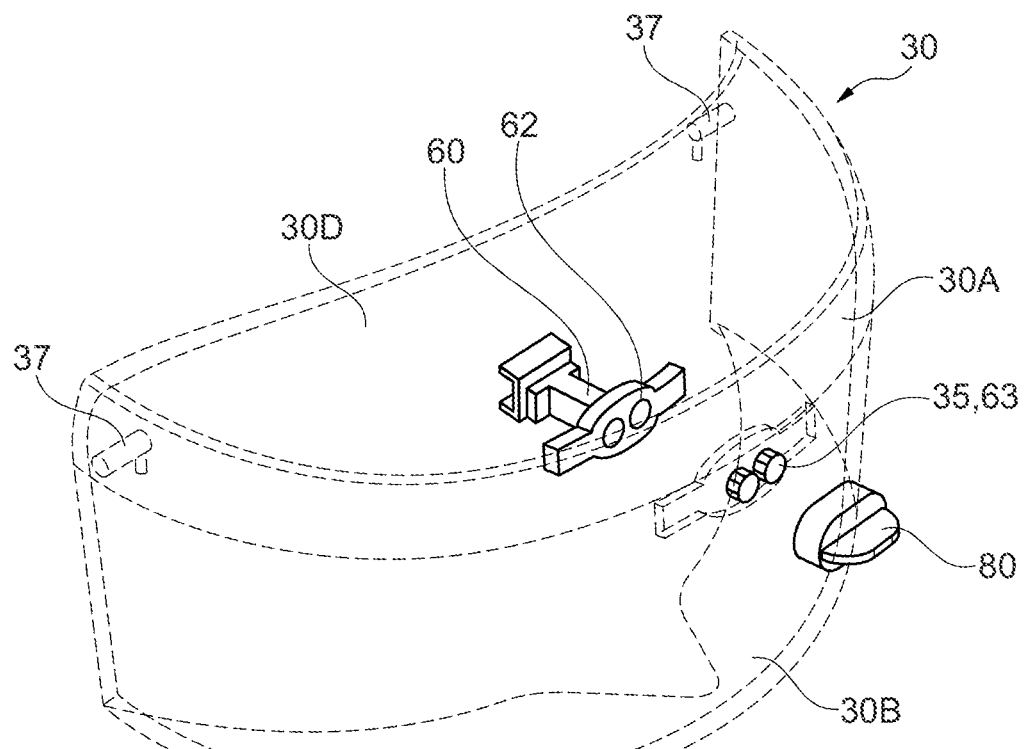
FIG. 8a illustrates another protective shield, according to an example embodiment.
Figure 8B:
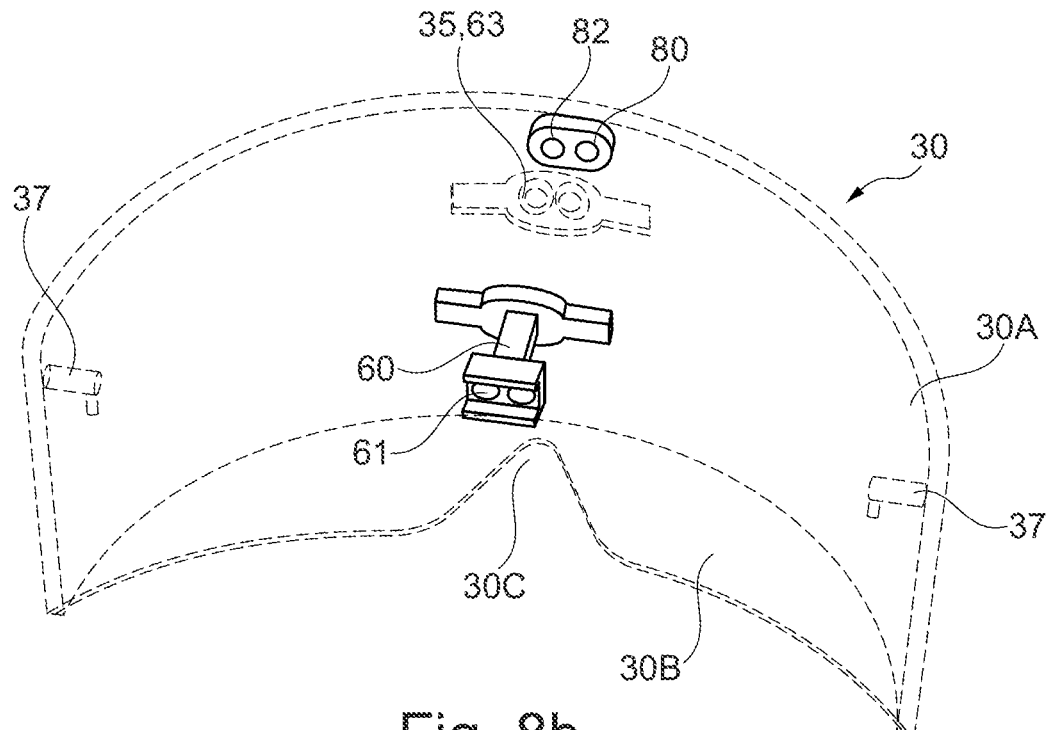
FIG. 8b illustrates a rear view of the protective shield of FIG. 8a, according to an example embodiment.

FIGS. 8a and 8b show a shield 30 for protection against laser radiation in various views. The shield 30 includes a curved main section 30A, a lower protection section 30B, and an upper protection section 30D. The main section 30A is in the shape of a segment of a lateral surface of a cylinder and is designed to cover the eyes of the wearer. The lower and upper protection sections 30B, 30D extend transversely or perpendicularly, respectively, to the main section 30A. The protection sections 30B, 30D are configured to be positioned below and above the eyes, respectively, and to be brought close to the face of the wearer.

This is to attenuate or prevent laser radiation coming from below or above from entering the eyes. The lower protection section 30B has a recess 30C for the wearer's nose.

The shield 30 is made of acrylic in the main section 30A and/or in the protection sections 30B, 30D, for example, and has a thickness of about 3.2 mm there.

Further, the shield 30 includes coupling elements 37 in the form of hooks. The hooks 37 are disposed on the main portion 30A on an inner side of the shield 30, that is, on the side facing the wearer. The hooks 37 can be hooked into temples of a glasses frame so that the shield 30 is carried by the glasses.

In addition, apertures 35 are provided in the shield 30 centrally in the main section 30A, i.e. in the area above the nose of the wearer. Magnets 63 are bonded into these. The magnets 63 are provided to interact with magnets 82 of an end cap 80 and magnets 62 of a spacer 60 to clamp the shield 30 between the end cap 80 and the spacer 60. The spacer 60 has further magnets 61 at an end remote from the shield 30, which are arranged to interact with magnets of, for example, a glasses frame. Thus, the shield 30 can be attached to glasses via the magnets and the spacer 60 in addition to the hooks 37.

This patent application claims the priority of German patent application DE 10 2020 112 737.5, the disclosure content of which is hereby incorporated by reference.

The invention claimed is:
1. An arrangement for protecting the face of a wearer, comprising
  a shield which is attachable to an auxiliary means,
  an intermediate member, and
  a first and second connecting means by which the shield is attachable to the auxiliary means,
    wherein the first connecting means is configured to directly attach the intermediate member to the auxiliary means by means of a reversible connection,
    wherein the second connecting means is configured to attach the shield to the intermediate member,
    wherein magnifying optics are attached to the auxiliary means,
    wherein a length of the intermediate member depends on a space requirement of the magnifying optics, and
    wherein the auxiliary means comprises a frame for glasses.
2. The arrangement according to claim 1, wherein the shield is disposable between the second connecting means and the intermediate member.
3. The arrangement according to claim 1, wherein the second connecting means and the intermediate member each have at least one magnet between which the shield can be arranged.
4. The arrangement according to claim 1, wherein the intermediate member has a first longitudinal end at which the first connecting means is arranged, the first connecting means comprising a first magnet, and a second longitudinal end at which a second magnet is arranged, wherein the first magnet can interact with a magnet of the auxiliary means, and wherein the second magnet can interact with a magnet of the second connecting means such that the shield is clampable between the second connecting means and the intermediate member via a magnetic connection and the intermediate member is clampable between the shield and the auxiliary means via a magnetic connection.

5. The arrangement according to claim 1, wherein the second connecting means can be arranged on a side of the shield facing away from the wearer.

6. The arrangement according to claim 1, wherein the auxiliary means is disposable between the wearer's face and the shield.

7. The arrangement according to claim 1, wherein the shield has a one-dimensional or two-dimensional curvature and/or the shape of a segment of a lateral surface of a cylinder.

8. The arrangement according to claim 1, wherein the shield is of a size such that the shield attached to the auxiliary means can extend over the face of the wearer or over the entire face of the wearer or beyond the entire face and below the chin following the outer contour of the head towards the neck of the wearer or can extend beyond the entire face following the outer contour of the head over at least a portion of the forehead area carrying the auxiliary means.

9. The arrangement according to claim 1, wherein the shield has a thickness of between 0.10 mm and 0.8 mm, and/or is made in one piece and/or has a weight of between 4 and 60 grams, preferably between 10 and 30 grams, and/or the shield comprises polycarbonate or an acetate film and/or is impermeable to liquids.

10. The arrangement according to claim 1, wherein the shield is stable in shape under its own weight or wherein the shield conforms to a planar support surface under its own weight and/or the shield comprises a thermoformed sheet, the thermoformed sheet defining a basic shape of the shield.

11. The arrangement according to claim 1, wherein the shield has at least one transparent section, the transparent section being arranged in a field of view, and/or the shield has an anti-reflective coating and/or an anti-fogging layer, which is arranged in each case on the side facing the wearer.

12. The arrangement according to claim 1, wherein the second connecting means comprises a light-emitting means and/or a camera.

* * * * *